US009485994B2

(12) United States Patent  (10) Patent No.: US 9,485,994 B2
Leveau et al.  (45) Date of Patent: Nov. 8, 2016

(54) SYNERGY-BASED BIOCONTROL OF PLANT PATHOGENS

(71) Applicant: The Regents of the University of California, Oakland, CA (US)

(72) Inventors: Johannes Henricus Josephus Leveau, Davis, CA (US); Hung Kim Doan, Davis, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 14/537,620

(22) Filed: Nov. 10, 2014

(65) Prior Publication Data

US 2015/0135371 A1  May 14, 2015

Related U.S. Application Data

(60) Provisional application No. 61/902,046, filed on Nov. 8, 2013.

(51) Int. Cl.
*A01N 63/00*  (2006.01)

(52) U.S. Cl.
CPC ..................................... *A01N 63/00* (2013.01)

(58) Field of Classification Search
None
See application file for complete search history.

(56) References Cited

U.S. PATENT DOCUMENTS

| | | | |
|---|---|---|---|
| 4,245,432 | A | 1/1981 | Dannelly |
| 4,272,417 | A | 6/1981 | Barke et al. |
| 4,808,430 | A | 2/1989 | Kouno |
| 5,645,831 | A | 7/1997 | Chilcott et al. |
| 5,876,739 | A | 3/1999 | Turnblad et al. |
| 9,131,699 | B2 | 9/2015 | Ano et al. |
| 2003/0176428 | A1 | 9/2003 | Schneidersmann et al. |

FOREIGN PATENT DOCUMENTS

| | | |
|---|---|---|
| WO | 98/21964 A1 | 5/1998 |
| WO | 98/21965 A1 | 5/1998 |
| WO | 98/21966 A2 | 5/1998 |
| WO | 98/21967 A1 | 5/1998 |
| WO | 98/50422 A1 | 11/1998 |
| WO | 99/09819 A1 | 3/1999 |
| WO | 99/09820 A1 | 3/1999 |
| WO | 99/10477 A1 | 3/1999 |
| WO | 00/58442 A1 | 10/2000 |
| WO | 02/28186 A2 | 4/2002 |
| WO | 02/080675 A1 | 10/2002 |
| WO | 2012/087980 A1 | 6/2012 |
| WO | 2013/178664 A1 | 12/2013 |

OTHER PUBLICATIONS

Axelrood et al., "Molecular characterization of bacterial diversity from British Columbia forest soils subjected to disturbance," *Canadian Journal of Microbiology*, 48(7):655-674 (2002).
Chow, et al., "Molecular characterization of bacterial diversity in Lodgepole pine (*Pinus contorta*) rhizosphere soils from British Columbia forest soils differing in disturbance and geographic source," *FEMS Microbiology Ecology*, 42(3): 347-357 (2002).
De Boer et al., "Anti-fungal properties of chitinolytic dune soil bacteria", *Soil Biology & Biochemistry*, 30(2): 193-203 (1998).
De Boer et al., "Growth of chitinolytic dune soil beta—subclass *Proteobacteria* in response to invading fungal hyphae", *Applied and Environmental Microbiology*, 67(8): 3358-3362 (2001).
De Boer et al., "*Collimonas fungivorans* gen. nov., sp. nov., a chitinolytic soil bacterium with the ability to grow on living fungal hypahe", *IJSEM*, 54(Pt 3):857-864 (2004).
Fritsche et al., "Identification and characterization of genes underlying hitinolysis in *Collimonas fungivorans* Ter331", *FEMS Microbiology Ecology*, 66(1): 123-135 (2008).
Hoppener-Ogawa et al., "Specific detection and real-time PCR quantification of potentially mycophagous bacteria belonging to the genus *Collimonas* in different soil ecosystems", *Appl Environ Microbiol.*, 73(13):4191-4197 (2007).
Hoppener-Ogawa et al., "*Collimonas arenae* sp. Nov. and *Collimonas pratensis* sp. nov., isolated from (semi-)natural grassland soils", *International Journal of Systematic and Evolutionary Microbiology*, 58: 414-419 (2008).
Hoppener-Ogawa et al., "Impact of *Collimonas* bacteria on community composition of soil fungi", *Environ Microbiol*, 11(6):1444-1452 (2009).
Hoppener-Ogawa et al., "Mycophagous growth of Collimonas bacteria in natural soils, impact on fungal biomass turnover and interactions with mycophagous Trichoderma fungi", ISME J, 3(2):190-198 (2009).
Kamilova et al., "Collimonas fungivorans, an unpredicted in vitro but efficient in vivo biocontrol agent for the suppression of tomato foot and root rot", *Environmental Microbiology*, 9(6): 1597-1603 (2007).
Leveau et al., "Genomic flank-sequencing of plasposon insertion sites for rapid identification of functional genes", *Journal of Microbiological Methods*, 66(2): 276-285 (2006).
Leveau et al., The bacterial genus *Collimonas*: mycophagy, weathering and other adaptive solutions to life in oligotropic soil environments, *Environ Microbiol*, 12(2):281-2 92 (2010).
Mela et al., "Comparative genomics of the pIPO2/pSB102 family of environmental plasmids: sequence, evolution, and ecology of pTer331 isolated from *Collimonas fungivorans* Ter331", *FEMS Microbiology Ecology*, 66(1): 45-62 (2008).
Mela et al., "Dual transcriptional profiling of a bacterial/fungal confrontation: Collimonas fungivorans versus Aspergillus niger", *ISME J* 5(9): 1494-1504 (2011).
Mela et al., "Comparative genomics of bacteria from the genus *Collimonas*: linking (dis)similarities in gene content to phenotypic variation and conservation", *Environmental Microbiology Reports* 4(4): 424-432 (2012).
Offre et al., Microdiversity of Burkholderiales associated with mycorrhizal and nonmycorrhizal roots of Medicago truncatula, *FEMS Microbiology Ecology* , 65(2): 180-192 (2008).
Postma et al., "Soil suppressiveness and functional diversity of the soil microflora in organic farming systems", *Soil Biology & Biochemistry*, 40(9): 2394-2406 (2008).
Uroz et al., "Efficient mineral weathering is a distinctive functional trait of the bacterial genus *Collimonas*", *Soil 2013Biology & Biochemistry* 41(10): 21782186 (2009).
Uroz et al., "Structure and function of bacterial communities in aging soils: insights from the Mendocino Ecological Staircase", 69: pp. 265-274, Soil Biology & Biochemistry (2014).

*Primary Examiner* — Alton Pryor
(74) *Attorney, Agent, or Firm* — Kilpatrick Townsend & Stockton LLP

(57) ABSTRACT

Methods and compositions are provided for control of pathogenic fungal or oomycetous infection.

39 Claims, 5 Drawing Sheets

SYNERGY-BASED BIOCONTROL OF PLANT PATHOGENS

CROSS-REFERENCES TO RELATED APPLICATIONS

This application claims priority to U.S. Provisional Application 61/902,046, filed Nov. 8, 2013, the contents of which are hereby incorporated in their entirety for all purposes.

BACKGROUND OF THE INVENTION

Fungal and oomycetous pathogens can cause significant damage to a wide variety of commercially important plant varieties including crops and ornamental plants. Such pathogens can kill plants, reduce yield, reduce plant strength (e.g., decrease resistance to lodging), cause symptoms of mineral deficiency, and predispose plants to infection by other pathogens. As such, there is great interest in developing compositions and methods for control of fungal and oomycetous pathogens.

Fungal and oomycetous pathogens are typically controlled by use of synthetic chemicals (e.g., fungicides). However, effective synthetic chemicals can be dangerous, toxic, and expensive. In some countries, certain fungicides or anti-oomycetous chemicals have been restricted or banned for these and other reasons. Therefore, there is great interest in developing fungal control methods and compositions that do not rely on synthetic chemical fungicides or anti-oomycetous compounds, or reduce the use of such chemicals.

Biocontrol agents are a promising candidate for reducing or eliminating the need for such chemicals. Biocontrol agents are typically microorganisms, such as bacteria, or one or more products thereof, that are applied to a plant or a plant propagation material (e.g., soil) to control a pathogen. However, there are a limited number of commercially available biocontrol agents. For these and other reasons, there remains a need to further develop methods and compositions containing biocontrol agents for the control of pathogenic fungi and Oomycetes.

BRIEF SUMMARY OF THE INVENTION

In a first aspect, the present invention provides a method of cultivating a plant resistant to a fungal or oomycetous infection comprising the steps of: a) contacting said plant with bacteria of the genus *Collimonas*, or a product thereof; and b) contacting said plant with bacteria of the genus *Bacillus*, or a product thereof, wherein said plant shows a greater resistance to the infection or exhibits reduced symptoms of fungal or oomycetous infection relative to a non-contacted plant. In some embodiments, the plant is cultivated in soil or other planting media that does not otherwise contain bacteria of the genus *Collimonas*. In some embodiments, said plant is a plant selected from the group consisting of tomato, potato, sweet potato, cassava, beets, ginger, horseradish, radish, ginseng, turnip, any root or tuber crop, pepper, eggplant, ground cherry, tomatillo, okra, other fruiting vegetables, cucumber cantaloupe, melon, muskmelon, squash, watermelon and other cucurbit plants.

In some embodiments, the part of said plant contacted with bacteria of the genus *Collimonas* or a product thereof is a root of said plant. In some embodiments, the part of said plant contacted with bacteria of the genus *Bacillus* or a product thereof is a root of said plant. In some embodiments, the part of said plant contacted with bacteria of the genus *Collimonas* or a product thereof is the seed of said plant. In some embodiments, the part of said plant contacted with bacteria of the genus *Bacillus* or a product thereof is the seed of said plant. In some embodiments, the part of said plant contacted with bacteria of the genus *Collimonas* or a product thereof is the foliage of said plant. In some embodiments, the part of said plant contacted with bacteria of the genus *Bacillus* or a product thereof is the foliage of said plant.

In some embodiments, the contacting of a) comprises contacting the plant with bacteria of the genus *Collimonas* and a product thereof. In some embodiments, the contacting of b) comprises contacting the plant with bacteria of the genus *Bacillus* and a product thereof. In some embodiments, the contacting of a) comprises contacting the plant with bacteria of the genus *Collimonas* and a product thereof, and the contacting of b) comprises contacting the plant with bacteria of the genus *Bacillus* and a product thereof.

In some embodiments, the fungal or oomycetous infection comprises an infection by a fungal pathogen from a class selected from the group consisting of Plasmodiophoromycetes, Oomycetes, Chytridiomycetes, Zygomycetes, Ascomycetes, Basidiomycetes, Deuteromycetes, Sordariomycetes, and combinations thereof. In some cases, the fungal or oomycetous pathogen is from the class Oomycetes. In some embodiments, said fungal or oomycetous infection comprises infection by a fungal pathogen from a genus selected from the group consisting of *Fusarium, Geotrichum, Aspergillus, Alternaria, Botryosphaeria, Colletotrichum, Magnaporthe, Verticillium, Cryphonectria, Botrytis, Monilinia, Sclerotium, Rhizoctonia*, and combinations thereof. In some embodiments, said fungal or oomycetous infection comprises infection by an Oomycete from a genus selected from the group consisting of *Pythium, Phytophthora*, and combinations thereof.

In some embodiments, said bacteria of the genus *Bacillus* comprise *Bacillus subtilis*. In some embodiments, said bacteria of the genus *Bacillus* comprise *Bacillus subtilis* var. *amyloliquefaciens*. In some embodiments, said bacteria of the genus *Bacillus* comprise *Bacillus subtilis* QST 713. In some embodiments, said bacteria of genus *Collimonas* comprise a species selected from the group consisting of *Collimonas arenae, Collimonas fungivorans*, and *Collimonas pratensis*. In some embodiments, said bacteria of genus *Collimonas* comprise *C. arenae* Cal35. In some embodiments, said bacteria of genus *Collimonas* comprise *C. arenae* Cal35 and said bacteria of the genus *Bacillus* comprise *Bacillus subtilis* QST 713.

In some embodiments, said bacteria of the genus *Collimonas* or a product thereof are in the form of a liquid suspension. In some embodiments, said bacteria of the genus *Collimonas* are in a liquid suspension at a concentration of approximately $1 \times 10^6$ cells per milliliter. In some embodiments, said bacteria of the genus *Bacillus* or a product thereof are in the form of a liquid suspension. In some embodiments, said bacteria of the genus *Bacillus* are in a liquid suspension with a concentration of approximately $1 \times 10^8$ or $1 \times 10^9$ colony forming units per gram.

In some embodiments, said contacting of a) or b) comprises a root dip. In some embodiments, said contacting of a) or b) comprises a soil drench. In some embodiments, said contacting of a) and b) comprises a root dip. In some embodiments, said contacting of a) and b) comprises a soil drench. In some embodiments, said contacting of a) and b) are independently selected from the group consisting of root dip, soil drench, and spray.

In a second aspect, the present invention provides a plant cultivated by any of the foregoing methods. In some embodiments, the present invention provides a plant in contact with bacteria from the genus *Bacillus* or a product thereof, and bacteria from the genus *Collimonas*, or a product thereof. In some embodiments, the plant is cultivated in soil that does not otherwise contain bacteria of the genus *Collimonas*.

In a third aspect, the present invention provides a composition of matter comprising: a) bacteria of the genus *Collimonas* or a product thereof; and b) bacteria of the genus *Bacillus* or a product thereof. In some embodiments, the composition comprises bacteria of the genus *Collimonas* and a product thereof. In some embodiments, the composition comprises bacteria of the genus *Bacillus* and a product thereof. In some embodiments, the composition comprises bacteria of the genus *Bacillus* and bacteria of the genus *Collimonas*, wherein the bacteria of the genus *Collimonas* are not naturally found in agricultural soil.

In some embodiments, said bacteria of the genus *Bacillus* comprise *Bacillus subtilis*. In some embodiments, said bacteria of the genus *Bacillus* comprise *Bacillus subtilis* QST 713. In some embodiments, said bacteria of genus *Collimonas* comprise a species selected from the group consisting of *Collimonas arenae*, *Collimonas fungivorans*, and *Collimonas pratensis*.

In some embodiments, said bacteria of the genus *Collimonas* are in the form of a liquid suspension. In some embodiments, said bacteria of the genus *Collimonas* are in a liquid suspension with a concentration of approximately $1\times10^6$ cells per milliliter. In some embodiments, said bacteria of the genus *Bacillus* are in the form of a liquid suspension. In some embodiments, said bacteria of the genus *Bacillus* are in a liquid suspension with a concentration of approximately $1\times10^8$ or $1\times10^9$ colony forming units per gram.

In a fourth aspect, the present invention provides a plant in contact with: a) bacteria of the genus *Collimonas* or a product thereof; and b) bacteria of the genus *Bacillus* or a product thereof. In some embodiments, the plant is a cultivated plant that is not naturally in contact with bacteria of the genus *Collimonas*.

DEFINITIONS

Unless defined otherwise, technical and scientific terms used herein have the same meaning as commonly understood by a person of ordinary skill in the art. See, e.g., Lackie, DICTIONARY OF CELL AND MOLECULAR BIOLOGY, Elsevier ($4^{th}$ ed. 2007); Sambrook et al., MOLECULAR CLONING, A LABORATORY MANUAL, Cold Springs Harbor Press (Cold Springs Harbor, N.Y. 1989); Raven et al. PLANT BIOLOGY ($7^{th}$ ed. 2004). Any methods, devices and materials similar or equivalent to those described herein can be used in the practice of this invention. The following definitions are provided to facilitate understanding of certain terms used frequently herein and are not meant to limit the scope of the present disclosure.

The term "plant" refers to a cultivated plant. The term "plant" includes whole plants, shoot vegetative organs/structures (e.g. leaves, stems and tubers), roots, flowers and floral organs/structures (e.g. bracts, sepals, petals, stamens, carpels, anthers and ovules), seed (including embryo, endosperm, and seed coat) and fruit (the mature ovary), plant tissue (e.g. vascular tissue, ground tissue, and the like) and cells (e.g. guard cells, egg cells, trichomes and the like), and progeny of same. The class of plants that can be used in the method of the invention is generally as broad as the class of higher and lower plants amenable to cultivation, including angiosperms (monocotyledonous and dicotyledonous plants), gymnosperms, and ferns. It includes plants of a variety of ploidy levels, including aneuploid, polyploid, diploid, haploid and hemizygous. Specific embodiments of plants useful for the methods and compositions of the present invention include but are not limited to commercial food crops, and energy crops.

The invention has use over broad range of plants, including species from the genera *Anacardium*, *Arabidopsis*, *Arachis*, *Asparagus*, *Atropa*, *Avena*, *Brassica*, *Citrus*, *Citrullus*, *Capsicum*, *Carthamus*, *Cocos*, *Coffea*, *Cucumis*, *Cucurbita*, *Daucus*, *Elaeis*, *Fragaria*, *Glycine*, *Gossypium*, *Helianthus*, *Heterocallis*, *Hordeum*, *Hyoscyamus*, *Lactuca*, *Linum*, *Lolium*, *Lycopersicon*, *Malus*, *Manihot*, *Majorana*, *Medicago*, *Nicotiana*, *Oryza*, *Panieum*, *Pannesetum*, *Persea*, *Phaesolus*, *Pistachia*, *Pisum*, *Pyrus*, *Prunus*, *Raphanus*, *Ricinus*, *Secale*, *Senecio*, *Sinapis*, *Solanum*, *Sorghum*, *Theobromus*, *Trigonella*, *Triticum*, *Vicia Vitis*, *Vigna*, and, *Zea*.

In some embodiments, the plant is selected from the group consisting of rice, maize, wheat, soybeans, cotton, canola, turfgrass, alfalfa, poplar, *eucalyptus*, switchgrass, sorghum, millet, *miscanthus*, sugarcane, pine, barley, tobacco, hemp, poppy, bamboo, canola, rape, sunflower, willow, or Brachypodium. In some embodiments, the plant selected from the group consisting of tomato, potato, sweet potato, cassava, beets, ginger, horseradish, radish, ginseng, turnip, any root or tuber crop, pepper, eggplant, ground cherry, tomatillo, okra, other fruiting vegetables, cucumber cantaloupe, melon, muskmelon, squash, watermelon and other cucurbit plants. In some embodiments, the plant is an ornamental plant. In some embodiments, the plant is a vegetable- or fruit-producing plant. In some embodiments, the plant is a monocot. In some embodiments, the plant is a dicot.

The term "plant" can refer to any potential plant propagation material. Such plant propagation material can include any generative part of a plant such as seeds and vegetative plant material such as cuttings and tubers (e.g., potatoes), which can be used for the multiplication of the plant. This includes seeds, roots, fruits, tubers, bulbs, rhizomes, shoots, sprouts and other parts of plants, including seedlings and young plants, which are to be transplanted after germination or after emergence from soil or other planting media. These young plants may also be protected before transplantation by a total or partial treatment by contacting with an anti-fungal or anti-oomycetous composition, such as any of the anti-fungal or anti-oomycetous compositions described herein.

The term "planting media" as used herein refers to any media that can support plant growth. The term includes soil, as well as media such as rock, wool, vermiculite, etc. The terms "soil" or "plant environment" for plants in the practice of the method of the present invention mean a support for use in culture of a plant and especially a support in which roots are to be grown. The terms are not limited in material quality, but include any material that may be used so far as a plant can be grown therein. For instance, so-called various soils, seedling mat, tapes, water or hydroponic solutions and the like can also be used. Specific examples of the material constituting the soil or cultivation carrier include, without limitation, sand, peat moss, perlite, vermiculite, cotton, paper, diatomaceous earth, agar, gelatinous materials, polymeric materials, rock wool, glass wool, wood chips, bark, pumice and the like. In some cases, the planting media is media that can support plant growth and does not naturally contain bacteria of the genus *Collimonas*.

As used herein, the term "fungus," "fungal pathogen," "fungi," and the like refers to a wide variety of nucleated organisms of the kingdom Fungi that can infect or otherwise injure a plant. Examples of fungi include yeasts, molds, mildews, and rusts.

As used herein the term "plant resistant to a fungal or oomycetous pathogen" refers to a plant that is resistant to infection by a fungal or oomycetous pathogen or resistant to the symptoms of fungal or oomycetous pathogen infection. For example, a plant resistant to a fungal or oomycetous pathogen can exhibit a lack of infection, or reduced symptoms of infection, when challenged with a pathogen. As another example, a plant resistant to a fungal or oomycetous pathogen can be infected by the fungal or oomycetous pathogen and yet exhibit a reduced number or degree of symptoms of said infection. As yet another example, a plant resistant to a fungal or oomycetous pathogen can be infected by the pathogen and exhibit one or more symptoms of infection by the pathogen and yet exhibit a reduction in an effect of the infection or symptom thereof. For instance, a plant resistant to a fungal or oomycetous pathogen can be infected by the pathogen, and exhibit one or more symptoms selected from the group consisting of leaf wilt, leaf or vascular discoloration (e.g., yellowing), and yet exhibit a reduction in yield loss in comparison to a plant that is not resistant to the fungal or oomycetous pathogen.

Accordingly, "enhanced resistance to a fungal or oomycetous pathogen" refers to a phenotype in which a plant has greater health, growth, multiplication, fertility, vigor, strength (e.g., lodging resistance), yield, or less severe symptoms of vascular discoloration during or after a fungal or oomycetous infection than an organism that does not have enhanced resistance to the pathogen. Where a plant is tested for resistance, a control plant could be a non-treated plant from the same plant line. The enhancement can be an increase of 0.1%, 0.2%, 0.3%, 0.5%, 0.75%, 1%, 1.5%, 2%, 3%, 4%, 5%, 6%, 7%, 8%, 9%, 10%, 12%, 15%, 17%, 20%, 25%, 30%, 35%, 40%, 50%, 60%, 70%, 80%, 90%, 100%, or more in health, growth, multiplication, fertility, vigor, strength (e.g., lodging resistance), or yield, as compared to a control plant. The enhancement can be a decrease of 0.1%, 0.2%, 0.3%, 0.5%, 0.75%, 1%, 1.5%, 2%, 3%, 4%, 5%, 6%, 7%, 8%, 9%, 10%, 12%, 15%, 17%, 20%, 25%, 30%, 35%, 40%, 50%, 60%, 70%, 80%, 90%, or 100% in vascular discoloration as compared to a control plant.

As used herein, the term "contacting" in the context of contacting a plant with a bacteria, or a product thereof, refers to any suitable method for bringing a bacteria, or a product thereof, in contact with the plant. Such methods include, but are not limited to, dipping, dripping, spraying, root dipping, soil drenching, dabbing, painting, coating, blotting, fumigating, irrigating, atomizing, or soil injection. The contacting can be applied to the plant directly. For example, a plant can be dipped or otherwise contacted with one or more bacteria or products thereof. The contacting can be performed prior to planting of the plant, after the planting of the plant, or during transfer of a plant from one planting media to another. Alternatively, the contacting can be applied to the plant indirectly. For example, a soil or other planting media can be contacted with one or more bacteria or products thereof, and the plant contacted with the soil or other planting media.

As used herein, the term "bacteria of the genus *Collimonas*" refers to bacteria from the *Collimonas* genus of bacteria in the family Oxalobacteraceae, order Burkholderiales. *Collimonas* can grow in slightly acidic sandy dune soils. *Collimonas* are generally not found in agricultural soils. The bacteria are characterized in their ability to hydrolyze the fungal cell wall component chitin. Species of *Collimonas* include but are not limited to *Collimonas arenae, Collimonas fungivorans*, and *Collimonas pratensis*. Strains of *Collimonas* include but are not limited to Ter strains, such as *C. fungivorans* Ter331, Ter14, or Ter6, *C. pratensis* Ter91, or *C. arenae* Ter10; or Cal strains, such as *C. arenae* Cal35, *C. fungivorans* Cal2, Cal1, or Cal39, or *C. pratensis* Cal31; or *Collimonas* sp. D-25. The *Collimonas* can be provided as a paste, a powder, a suspension in liquid, a colony, a streak, a stab, or in any other suitable manner.

As used herein the term "bacteria of the genus *Bacillus*" refers to bacteria from the *Bacillus* genus of bacteria in the family Bacillaceae, order Bacillales. Species of *Bacillus* include but are not limited to *Bacillus subtilis*. Strains of *Bacillus* include but are not limited to *Bacillus subtilis* var. *amyloliquefaciens* and *Bacillus subtilis* QST 713. Additional species and strains of *Bacillus* are described herein. The *Bacillus* can be provided as a paste, a powder, a suspension in liquid, a colony, a streak, a stab, or in any other suitable manner.

As used herein, the term "product thereof" in reference to a bacteria of the genus *Collimonas* or *Bacillus* refers to one or more primary or secondary metabolites of the bacteria. For example, the product thereof can be an anti-fungal or anti-oomycetous agent produced by the bacteria. Such anti-fungal or anti-oomycetous agents include, but are not limited to small molecule anti-fungal agents such as lipopeptides, cyclic lipopeptides, bacilysin, chlorotetain, iturin A, fengycin, surfactins, and surfactin A. In some cases, such anti-fungal or anti-oomycetous agents can include hydrolases, such as proteases, or enzymes that hydrolyze chitin. Alternatively, the products thereof can provide enhanced plant vigor or growth, thus allowing the plant to mount a stronger defense against a fungal or oomycetous pathogen. For example, the products thereof can include phytic acid, favorable for freeing phosphate from soil, thus facilitating plant absorption and leading to enhanced plant vigor.

DETAILED DESCRIPTION

Figure 1:
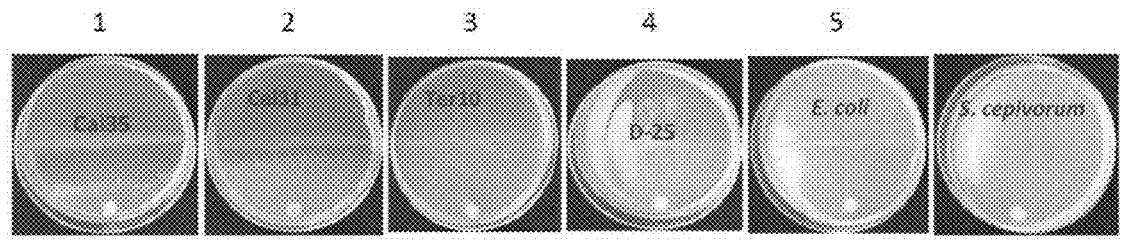
FIG. 1. Representative photographs of confrontation plates showing the scale that was used to score mycelial growth of fungi/Oomycetes in the presence of different bacterial strains. Shown here are 5 bacteria in confrontation with *Sclerotium cepivorum* on WYA plates. The plate on the far right is a control, with no bacteria inoculated across the center of the agar surface. Scores range on a scale of 1 (near-complete inhibition of mycelial growth) to 5 (mycelial growth not at all affected).

Described herein are methods and compositions for biocontrol of fungal or oomycetous pathogens. In some embodiments, a composition can contain a *Collimonas* bacteria or a product thereof. In some embodiments, the composition can contain a *Bacillus* bacteria or a product thereof. In some embodiments, the composition can contain a *Collimonas* bacteria or a product thereof and a *Bacillus* bacteria or a product thereof. In some cases, such compositions can provide synergistic control of fungal or oomycetous pathogens when contacted with a cultivated plant. Such compositions generally do not contact a cultivated plant in nature because *Collimonas* are not naturally found in agricultural soils or other planting media. See, de Boer et al., IJSEM. 2004 May; 54(Pt 3):857-64. In some cases, agricultural soils are soils that do not contain detectable amounts of naturally occurring bacteria of the genus *Collimonas*.

I. Compositions

Compositions described herein contain one or more biocontrol agents. The biocontrol agents can include bacteria from the genus *Bacillus*, or one or more products thereof. The biocontrol agents can include bacteria from the genus *Collimonas*, or one or more products thereof. The biocontrol agents can include bacteria from the genus *Bacillus*, or one or more products thereof, and bacteria from the genus *Collimonas*, or one or more products thereof.

For example, the biocontrol agent can contain *Collimonas* bacteria and one or more products of *Bacillus*. As another example, the biocontrol agent can contain *Bacillus* bacteria and one or more products of *Collimonas*. As yet another example, the biocontrol agent can contain *Collimonas* bacteria and one or more products thereof and one or more products of *Bacillus*. As yet another example, the biocontrol agent can contain bacteria from the genus *Bacillus* and one or more products thereof, and bacteria from the genus *Collimonas* and one or more products thereof.

For example, the composition can be a mixture of i) a pure or substantially pure *Bacillus* culture and ii) a pure or substantially pure *Collimonas* culture. In some cases, the cultures are separated from a growth media (e.g., by centrifugation or filtering) and mixed in or on a sterile liquid or solid medium. In some cases, the sterile liquid or solid medium can be, or contain, spent media (e.g., sterilized spent media), or one or more products derived therefrom. In some cases, the cultures, including spent media are mixed together to obtain a composition described herein. In some cases, a *Bacillus* culture is harvested and mixed into a *Collimonas* culture. In some cases, a *Collimonas* culture is harvested and mixed into a *Bacillus* culture.

Generally, the bacteria are pure or substantially pure. For example, the bacteria can be in a powder or liquid suspension that contains no, or substantially no, other living microorganisms. For instance, the bacteria can represent at least 90%, 95%, 99%, 99.9%, or more of the living prokaryotic organisms in a powder, liquid suspension, or other suitable carrier, medium, or agricultural formulation.

The one or more products of *Bacillus* or *Collimonas* can be obtained from bacteria or spent media. For example, the products can be obtained by culturing the bacteria with culture media (e.g. liquid or solid media) to obtain cultured bacteria and spent media. In some cases, the composition is, or contains, spent media, or one or more purified components thereof. In some cases, the spent media is harvested by separating the media from the bacteria. In some cases, bacterial products thereof are purified from the bacteria or the spent media. For example, bacteria can be lysed and one or more products thereof can be purified. Alternatively, the spent media can be harvested and bacterial products can be purified from the spent media. In some cases, the composition does not contain spent media. In some cases, bacteria are cultured, spent media is harvested and optionally sterilized (e.g., by filtration, addition of anti-biotic agents, or heat treatment, such as with an autoclave), and then mixed with the bacteria to provide a liquid suspension.

In some embodiments, products of one or more *Bacillus* or *Collimonas* bacteria can include metabolites produced by the microorganisms including, but not limited to, antibiotics, enzymes, siderophores or growth promoting agents. Such metabolites can include, for example, zwittermicin A, kanosamine, polyoxine, enzymes such as alpha-amylase, chitinases, and pectinases, phytohormones and precursors thereof, such as auxins, gibberellin-like substances, cytokinin-like compounds, lipopeptides such as iturins, plipastatins, or surfactins, e.g. agrastatin A, bacillomycin D, bacilysin, difficidin, macrolactin, fengycin, bacilysin, plipastatin A, plipastatin B, and bacilaene. In some cases, the metabolites are lipopeptides, such as those produced by *Bacillus pumilis* (NRRL Accession No, B-30087) or *Bacillus subtilis* AQ713 (NRRL Accession No. B-21661). In some cases, the metabolites are iturin A, surfactin A, plipastatin A, or agrastatin A.

In some cases, the composition contains spent media from *Bacillus*, or one or more purified components thereof. In some cases, the composition contains spent media from *Collimonas*, or one or more purified components thereof. In some cases, the composition contains spent media from *Bacillus* and *Collimonas*, or one or more purified components from *Bacillus* or *Collimonas* or from both *Collimonas* and *Bacillus*. In some cases, the composition contains spent media from *Collimonas* but does not contain spent media from *Bacillus*. In some cases, the composition contains spent media from *Bacillus*, but does not contain spent media from *Collimonas*.

In some cases, the composition comprises cultures (e.g., isolated pure cultures) of one or more *Bacillus* and one or more *Collimonas* bacteria, or products thereof. In some cases, the composition comprises bacterial suspensions in a whole broth culture or a metabolite containing supernatant or purified metabolite obtained from whole broth culture of one or more *Bacillus* or *Collimonas*.

The bacteria or products thereof can be in a liquid (e.g., a solution or suspension) or solid form. Exemplary solid forms include but are not limited to a powder or a paste. The bacteria can be in an otherwise sterile carrier or medium. The medium can be liquid (e.g., a solution or suspension of bacteria) or solid (e.g., a powder or paste).

The chemical or physical properties of a liquid (e.g., solution or suspension) containing bacteria and/or products thereof can be adjusted using methods known in the art. For example, the liquid can be adjusted to increase the shelf life (e.g., increase stability of anti-fungal properties over time) of the composition. In some cases, the pH or isotonic strength of the suspension can be adjusted by addition of acids, bases, salts, or water to the suspension. As another example, stabilizing agents such as enzyme (e.g., protease) inhibitors or antibiotics can be added to the suspension. In some cases, the volume or amount of liquid can be adjusted to obtain a concentration of one or more of *Collimonas* or *Bacillus* bacteria or products thereof. In some cases, the liquid further contains surfactants. In some cases, the liquid further contains plant nutrients or micronutrients, including but not limited to nitrogen or phosphorous. In some cases, the liquid is pH adjusted before or after addition of bacteria or products thereof. In some cases, the liquid contains one or more pH buffering agents.

For example, the bacteria can be in the form of colonies, a streak, or a stab on an otherwise sterile medium, such as agar. As another example, the bacteria can be in the form of a powder mixed with a water soluble medium such as whey, maltodextrin, maltodextrin M100, etc. The powder can include a moisture binding agent or dessicant to reduce clumping or increase the ease of handling. Such moisture binding agents or dessicants include, but are not limited to silica, balith, or calcium chloride. As another example, the bacteria, or one or more products thereof, can be mixed with planting media. For example, the bacteria or one or more products thereof can be mixed with sterile soil. In some cases, the solid medium further contains surfactants. In some cases, the solid medium further contains plant nutrients or micronutrients, including but not limited to nitrogen or phosphorous. In some cases, the solid medium is pH adjusted before or after addition of bacteria or products thereof. In some cases, the solid medium contains one or more pH buffering agents. In some cases, the volume or amount of solid media can be adjusted to obtain a concentration of one or more of *Collimonas* or *Bacillus* bacteria or products thereof.

Exemplary concentrations of *Bacillus* in a composition of the present invention can include, but are not limited to, $1 \times 10^3$ colony forming units/g (cfu/g), $1 \times 10^4$ cfu/g, $1 \times 10^5$ cfu/g, $1 \times 10^6$ cfu/g, $1 \times 10^7$ cfu/g, $1 \times 10^8$ cfu/g, $1 \times 10^9$ cfu/g, $1 \times 10^{10}$ cfu/g, $1 \times 10^{11}$ cfu/g or $1 \times 10^{12}$ cfu/g. Exemplary concentrations of *Bacillus* in a composition of the present invention can include, but are not limited to, $1 \times 10^3$-$1 \times 10^{12}$ cfu/g, $1 \times 10^4$-$1 \times 10^{11}$ cfu/g, $1 \times 10^5$-$1 \times 10^{10}$ cfu/g, $1 \times 10^6$-$1 \times 10^9$ cfu/g, or $1 \times 10^6$-$1 \times 10^8$ cfu/g. Exemplary concentrations of *Bacillus* in a composition of the present invention can include, but are not limited to, $1 \times 10^3$ cells/mL, $1 \times 10^4$ cells/mL, $1 \times 10^5$ cells/mL, $1 \times 10^6$ cells/mL, $1 \times 10^7$ cells/mL, $1 \times 10^8$ cells/mL, $1 \times 10^9$ cells/mL, $1 \times 10^{10}$ cells/mL, $1 \times 10^{11}$ cells/mL or $1 \times 10^{12}$ cells/mL. Exemplary concentrations of *Bacillus* in a composition of the present invention can include, but are not limited to, $1 \times 10^3$-$1 \times 10^{12}$ cells/mL, $1 \times 10^4$-$1 \times 10^{11}$ cells/mL, $1 \times 10^5$-$1 \times 10^{10}$ cells/mL, $1 \times 10^6$-$1 \times 10^9$ cells/mL, or $1 \times 10^6$-$1 \times 10^8$ cells/mL.

Exemplary concentrations of *Collimonas* in a composition of the present invention can include, but are not limited to, $1 \times 10^3$ colony forming units/g (cfu/g), $1 \times 10^4$ cfu/g, $1 \times 10^5$ cfu/g, $1 \times 10^6$ cfu/g, $1 \times 10^7$ cfu/g, $1 \times 10^8$ cfu/g, $1 \times 10^9$ cfu/g, $1 \times 10^{10}$ cfu/g, $1 \times 10^{11}$ cfu/g or $1 \times 10^{12}$ cfu/g. Exemplary concentrations of *Collimonas* in a composition of the present invention can include, but are not limited to, $1 \times 10^3$-$1 \times 10^{12}$ cfu/g, $1 \times 10^4$-$1 \times 10^{11}$ cfu/g, $1 \times 10^5$-$1 \times 10^{10}$ cfu/g, $1 \times 10^6$-$1 \times 10^9$ cfu/g, or $1 \times 10^6$-$1 \times 10^8$ cfu/g. Exemplary concentrations of *Collimonas* in a composition of the present invention can include, but are not limited to, $1 \times 10^3$ cells/mL, $1 \times 10^4$ cells/mL, $1 \times 10^5$ cells/mL, $1 \times 10^6$ cells/mL, $1 \times 10^7$ cells/mL, $1 \times 10^8$ cells/mL, $1 \times 10^9$ cells/mL, $1 \times 10^{10}$ cells/mL, $1 \times 10^{11}$ cells/mL or $1 \times 10^{12}$ cells/mL. Exemplary concentrations of *Collimonas* in a composition of the present invention can include, but are not limited to, $1 \times 10^3$-$1 \times 10^{12}$ cells/mL, $1 \times 10^4$-$1 \times 10^{11}$ cells/mL, $1 \times 10^5$-$1 \times 10^{10}$ cells/mL, $1 \times 10^6$-$1 \times 10^9$ cells/mL, or $1 \times 10^6$-$1 \times 10^8$ cells/mL.

Compositions of the present invention may include formulation inerts added to compositions comprising cells, cell-free preparations or metabolites to improve efficacy, stability, or usability and/or to facilitate processing, packaging or end-use application. Such formulation inerts and ingredients may include carriers, stabilization agents, nutrients, or physical property modifying agents, which may be added individually or in combination. In some embodiments, the carriers may include liquid materials such as water, oil, and other organic or inorganic solvents and solid materials such as minerals, polymers, or polymer complexes derived biologically or by chemical synthesis. In some embodiments, the carrier is a binder or adhesive that facilitates adherence of the composition to a plant part, such as a seed or root. See, for example, Taylor, A. G., et al., "Concepts and Technologies of Selected Seed Treatments", Anna. ev. Phytopathol. 28: 321-339 (1990). The stabilization agents may include anti-caking agents, anti-oxidation agents, dessicants, protectants or preservatives. The nutrients may include carbon, nitrogen, or phosphors sources such as sugars, polysaccharides, oil, proteins, amino acids, fatty acids or phosphates. The physical property modifiers may include bulking agents, wetting agents, thickeners, pH modifiers, rheology modifiers, dispersants, adjuvants, surfactants, antifreeze agents or colorants. In some embodiments, the composition comprising cells, cell-free preparations or metabolites produced by fermentation can be used directly with or without water as the diluent without any other formulation preparation. In some embodiments, the formulation inerts are added after concentrating fermentation broth and during and/or after drying.

In some cases, the *Bacillus* are in an endospore form. In some cases, the *Bacillus* are not in an endospore form. In some cases, the *Bacillus* are in a mixture of endospore and vegetative states. In some cases, at least about 1% of the *Bacillus* are in an endospore state and less than about 99% are in a vegetative state. In some cases, at least about 99% of the *Bacillus* are in a vegetative state and less than about 1% are in an endospore state. In some cases, 1%, 2%, 3%, 4%, 5%, 6%, 7%, 8%, 9%, 10%, 12%, 15%, 20%, 25%, 30%, 35%, 40%, 45%, 50%, 55%, 60%, 65%, 70%, 80%, 90%, 95%, 99%, or more of the *Bacillus* are in an endospore state. In some cases, 1%, 2%, 3%, 4%, 5%, 6%, 7%, 8%, 9%, 10%, 12%, 15%, 20%, 25%, 30%, 35%, 40%, 45%, 50%, 55%, 60%, 65%, 70%, 80%, 90%, 95%, 99%, or more of the *Bacillus* are in a vegetative state.

Biocontrol agents can be applied in combination with synthetic chemicals, such as pesticides, nematicides, miticides, or fungicides. In some cases, a biocontrol agent containing *Collimonas* or a product thereof and *Bacillus* or a product thereof can be mixed with one or more other chemical and non-chemical additives, adjuvants or treatments, wherein such treatments include but are not limited to chemical and non-chemical fungicides, insecticides, miticides, nematicides, fertilizers, nutrients, minerals, auxins, growth stimulants and the like. In some cases, the biocontrol agent allows the use of a lower amount of synthetic chemical to obtain the same degree of pathogen control.

The present invention is directed to a composition comprising at least one *Bacillus* bacteria selected from the group consisting of *Bacillus chitinosporous* AQ746 (NRRL Accession No. B-21618), *Bacillus mycoides* AQ726 (NRRL Accession No. B-21664), *Bacillus pumilus* (NRRL Accession No. B-30087), *Bacillus pumilus* AQ717 (NRRL Accession No. B-21662), *Bacillus* sp. AQ175 (ATCC Accession No. 55608), *Bacillus* sp. AQ177 (ATCC Accession No. 55609), *Bacillus* sp, AQ178 (ATCC Accession No. 53522), *Bacillus subtilis* AQ743 (NRRL Accession No. B-21665), *Bacillus subtilis* AQ713 (NRRL Accession No. B-21661), *Bacillus subtilis* AQ153 (ATCC Accession No. 55614), *Bacillus thuringiensis* BD#32 (NRRL Accession No. B-21 30), *Bacillus thuringiensis* AQ52 (NRRL Accession No. B-21 619), *Bacillus thuringiensis* subspec. *kurstaki* BMP 123, *Bacillus subtilis* AQ30002 (NRRL Accession No. B-50421), and *Bacillus subtilis* AG 30004 (NRRL Accession No. B-50455) and/or a mutant or variant of one or more of these strains, and/or a metabolite produced by the respective strain that exhibits activity (e.g., synergistic activity) against a fungal or oomycetous pathogen when contacted with a plant simultaneously or sequentially with a composition containing a *Collimonas* bacteria or a product thereof. In some cases, the *Bacillus* is a wild-type, mutant, or variant of one or more of the foregoing strains, and/or a metabolite produced by the respective strain that exhibits activity (e.g., synergistic activity) against a fungal and an oomycetous pathogen when contacted with a plant simultaneously or sequentially with a *Collimonas* bacteria or a product thereof. In some cases, the composition contains a mixture of one or more of the foregoing *Bacillus* bacteria, a mutant of such bacteria, or one or more products thereof. In some cases, one or more *Bacillus* bacteria in the composition are recombinant bacteria. In some cases, the composition contains a product of a recombinant *Bacillus* bacteria.

In some cases, the *Bacillus* is, or is derived from, a commercial biocontrol agent such as a Serenade product from AgraQuest, e.g., Serenade ASO, Serenade Biofungicide, Serenade Garden Disease, Serenade Max, or Serenade Soil. In some cases, the *Bacillus* is, or is derived from, a commercial biocontrol agent such as EcoGuard Biofungicide or Green Releaf from Novozymes Biologicals. In some cases, the *Bacillus* is, or is derived from, a commercial biocontrol agent such as Kodiak from Bayer Crop Science. In some cases, the *Bacillus* is, or is derived from, a commercial biocontrol agent such as Taegro from Novozymes. Other *Bacillus* based commercial biocontrol agents are known in the art, and the *Bacillus* can be, or can be derived from, one or more such commercial *Bacillus* based biocontrol agents.

Additional strains of *Bacillus* include, but are not limited to, those described in WO 2013/178664; WO 98/21966; WO 99/09820; WO 00/58442; WO 99/10477; WO 98/21967; WO 99/09819; WO 98/50422; WO 98/21964; U.S. Pat. No. 5,645,831; WO 98/21965; and WO 2012/087980, each of which are hereby incorporated by reference in their entirety for all purposes. In some cases, the *Bacillus* is a wild-type, mutant, or variant of one or more of the foregoing strains, and/or a metabolite produced by the respective strain that exhibits activity (e.g., synergistic activity) against a fungal or oomycetous pathogen when contacted with a plant simultaneously or sequentially with a *Collimonas* bacteria or a product thereof.

The present invention is directed to a composition comprising at least one *Collimonas* bacteria selected from the group consisting of *Collimonas arenae, Collimonas fungivorans,* and *Collimonas pratensis.* In some cases, the *Collimonas* is a Ter strain. In some cases, the *Collimonas* is a Cal strain. In some cases, the *Collimonas* is a strain of *C. arenae.* In some cases, the *C. arenae* strain is Cal35. In some cases, the *Collimonas* is a Cal31 strain. In some cases, the *Collimonas* is a Cal35 strain. In some cases, the *Collimonas* is a Cal39 strain. In some cases, the *Collimonas* is a Cal1 strain. In some cases, the *Collimonas* is a Cal2 strain. In some cases, the *Collimonas* is a Ter6 strain. In some cases, the *Collimonas* is a Ter10 strain. In some cases, the *Collimonas* is a Ter14 strain. In some cases, the *Collimonas* is a Ter331 strain. In some cases, the *Collimonas* is a D-25 strain. In some cases, the *Collimonas* is a *Collimonas* bacteria described in Leveau et al., Environ Microbiol. 2010 February; 12(2):281-92; Höppener-Ogawa et al., Environ Microbiol. 2009 June; 11(6):1444-52; or Höppener-Ogawa et al., ISME J. 2009 February; 3(2):190-8. In some cases, the *Collimonas* is a wild-type, mutant, or variant of one or more of the foregoing strains, and/or a metabolite produced by the respective strain that exhibits activity (e.g., synergistic activity) against a fungal or oomycetous pathogen when contacted with a plant simultaneously or sequentially with a *Bacillus* bacteria or a product thereof. In some cases, the *Collimonas* is a wild-type, mutant, or variant of one or more of the foregoing strains, and/or a metabolite produced by the respective strain that exhibits activity (e.g., synergistic activity) against a fungal and an oomycetous pathogen when contacted with a plant simultaneously or sequentially with a *Bacillus* bacteria or a product thereof. In some cases, the composition contains a mixture of one or more of the foregoing *Collimonas* bacteria, a mutant of such bacteria, or one or more products thereof. In some cases, one or more *Collimonas* bacteria in the composition are recombinant bacteria. In some cases, the composition contains a product of a recombinant *Collimonas* bacteria.

Compositions of the present invention can provide synergistic control of fungal or oomycetous pathogens. As used herein, the term "synergistic" when used in the context of fungal pathogen control can refer to the anti-fungal or anti-oomycetous activity of a composition containing a *Bacillus* bacteria or a product thereof and a *Collimonas* bacteria or a product thereof, wherein the composition is more effective (e.g., statistically significantly more effective) against a fungal or oomycetous pathogen than one or more, or any, of the individual components.

A "variant" is a strain having all the identifying characteristics of the parent organism as indicated in this text and can be identified as having a genome that hybridizes under conditions of high stringency to the genome of the parent organism.

"Hybridization" refers to a reaction in which one or more polynucleotides react to form a complex that is stabilized via hydrogen bonding between the bases of the nucleotide residues. The hydrogen bonding may occur by Watson-Crick base pairing, Hoogstein binding, or in any other sequence-specific manner. The complex may comprise two strands forming a duplex structure, three or more strands forming a multi-stranded complex, a single self-hybridizing strand, or any combination of these. Hybridization reactions can be performed under conditions of different "stringency." In general, a tow stringency hybridization reaction is carried out at about 40° C. in 10×SSC or a solution of equivalent ionic strength/temperature. A moderate stringency hybridization is typically performed at about 50° C. in 6×SSC, and a high stringency hybridization reaction is generally performed at about 60° C. in 1×SSC.

A variant of an indicated microorganism (e.g., a microorganism indicated by an NRRL or ATCC Accession Number, or a strain designation) may also be defined as a strain having a genomic sequence that is greater than 85%, more preferably greater than 90% or more preferably greater than 95% sequence identity to the genome of the indicated organism. A polynucleotide or polynucleotide region (or a polypeptide or polypeptide region) has a certain percentage (for example, 80%, 85%, 90%, or 95%) of "sequence identity" to another sequence means that, when aligned, that percentage of bases (or amino acids) are the same in comparing the two sequences. This alignment and the percent homology or sequence identity can be determined using software programs known in the art, for example, those described in Current Protocols in Molecular Biology (F. M, Ausubel et al. eds., 1987) Supplement 30, section 7.7.18, Table 7.7.1.

Compositions of the present invention can be used for control of a wide variety of fungal or oomycetous pathogens. The fungal or oomycetous pathogens can be one or more fungi or Oomycetes from a class selected from the group consisting of Plasmodiophoromycetes, Oomycetes, Chytridiomycetes, Zygomycetes, Ascomycetes, Basidiomycetes, Deuteromycetes, and Sordariomycetes. The fungal or oomycetous pathogens can be one or more fungi from a genus selected from the group consisting of *Fusarium, Geotrichum, Aspergillus, Alternaria, Botryosphaeria, Colletotrichum, Magnaporthe, Verticillium, Cryphonectria, Botrytis, Monilinia, Sclerotium*, and *Rhizoctonia*. The fungal or oomycetous pathogen can be from the class Oomycetes (synonym Peronosporomycetes). In some cases, the fungal pathogen is *Fusarium oxysporum*. In some cases, the fungal pathogen is *Fusarium oxysporum* f. sp. *lycopersici* (Fol) race 3. In some cases, the *Fusarium oxysporum* f. sp. *lycopersici* (Fol) race 3 is strain D11 or D12, or a variant thereof.

II. Formulations

Described herein are compositions as described above and additionally comprising at least one additional component selected from the group consisting of extenders, solvents, spontaneity promoters, carriers, emulsifiers, dispersants, frost protectants, thickeners, and adjuvants. These compositions are referred to as formulations.

Described herein are formulations for application of one or more compositions of the present invention to a plant or planting media. In one aspect, such formulations, and application forms prepared from them, are provided as crop protection agents and/or fungicidal agents, such as drench, drip and spray liquors, comprising a composition of the invention. The application forms may comprise further crop protection agents and/or pesticidal agents, and/or activity-enhancing adjuvants such as penetrants. For example, such application forms can comprise vegetable oils such as, for example, rapeseed oil, sunflower oil, mineral oils such as, for example, liquid paraffins, alkyl esters of vegetable fatty acids, such as rapeseed oil or soybean oil methyl esters, or alkanol alkoxylates, and/or spreaders such as, for example, alkylsiloxanes and/or salts, examples being organic or inorganic ammonium or phosphonium salts, examples being ammonium sulphate or diamonium hydrogen phosphate, and/or retention promoters such as dioctyl sulphosuccinate or hydroxypropylguar polymers and/or humectants such as glycerol and/or fertilizers such as ammonium, potassium or phosphorous fertilizers, for example.

Examples of typical formulations include water-soluble liquids (SL), emulsifiable concentrates (EC), emulsions in water (EW), suspension concentrates (SC, SE, FS, OD), water-dispersible granules (WG), granules (G) and capsule concentrates (CS); these and other possible types of formulation are described, for example, by Crop Life International and in Pesticide Specifications, Manual on development and use of FAO and WHO specifications for pesticides, FAO Plant Production and Protection Papers—1 73, prepared by the FAO/WHQ Joint Meeting on Pesticide Specifications, 2004, ISBN: 9251 048576. The formulations may comprise active agrochemical compounds other than one or more active components of the invention (e.g., other than *Collimonas* or a product thereof and *Bacillus* or a product thereof).

The formulations or application forms in question preferably comprise auxiliaries, such as extenders, solvents, spontaneity promoters, carriers, emulsifiers, dispersants, frost protectants, biocides, thickeners and/or other auxiliaries, such as adjuvants, for example. An adjuvant in this context is a component which enhances the biological effect of the formulation, without the component itself having a biological effect. Examples of adjuvants are agents which promote the retention, spreading, attachment to the plant or penetration of the plant surface (e.g., penetration of the root, shoot, or leaf surface).

Suitable extenders are, for example, water, polar and nonpolar organic chemical liquids, for example from the classes of the aromatic and non-aromatic hydrocarbons (such as paraffins, alkylbenzenes, alkylnaphthalenes, or chlorobenzenes), the alcohols and polyols (which, if appropriate, may also be substituted, etherified and/or esterified), the ketones (such as acetone, cyclohexanone), esters (including fats and oils) and (poly)ethers, the unsubstituted and substituted amines, amides, lactams (such as N-alkylpyrrolidones) and lactones, the sulphones and sulphoxides (such as dimethyl sulphoxide).

If the extender used is water, it is also possible to employ, for example, organic solvents as auxiliary solvents. Suitable liquid solvents include, but are not limited to: aromatics such as xylene, toluene or alkylnaphthalenes, chlorinated aromatics or chlorinated aliphatic hydrocarbons such as chlorobenzenes, chloroethylenes or methylene chloride, aliphatic hydrocarbons such as cyclohexane or paraffins, for example petroleum fractions, mineral or vegetable oils, alcohols such as butanol or glycol and also their ethers and esters, ketones such as acetone, methyl ethyl ketone, methyl isobutyl ketone or cyclohexanone, strongly polar solvents such as dimethyl formamide or dimethyl sulphoxide, or water.

Any suitable carrier may in principle be used. Suitable carriers can include, for example, ammonium salts and ground natural minerals such as kaolins, clays, talc, chalk, quartz, attapulgite, montmorillonite, or diatomaceous earth, or ground synthetic minerals, such as finely divided silica, alumina or natural or synthetic silicates, resins, waxes and/or solid fertilizers. Mixtures of such carriers may likewise be used. Carriers suitable for granules include the following; for example, crushed or fractionated natural minerals such as calcite, marble, pumice, sepiolite, dolomite, or synthetic granules of inorganic and organic meals, or granules of organic material such as sawdust, paper, coconut shells, maize cobs or tobacco stalks.

Examples of emulsifiers and/or foam-formers, dispersants or wetting agents having ionic or nonionic properties, or mixtures of these surface-active substances, are salts of polyacrylic acid, salts of lignosulphonic acid, salts of phenolsulphonic acid or naphthalenesulphonic acid, polycondensates of ethylene oxide with fatty alcohols or with fatty acids or with fatty amines, with substituted phenols (preferably alkylphenois or arylphenols), salts of sulphosuccinic esters, taurine derivatives (preferably alkyltaurates), phosphoric esters of polyethoxylated alcohols or phenols, fatty acid esters of polyols, or derivatives of the compounds containing sulphates, sulphonates, phosphates, or phosphonates, examples being alkylaryl polyglycol ethers, alkylsulphonates, alkyl sulphates, arylsulphonates, protein hydrolysates, lignin-sulphite waste liquors and methylcellulose.

Further auxiliaries that may be present in the formulations and in the application forms derived from them include colorants such as inorganic pigments, examples being iron oxide, titanium oxide, Prussian Blue, and organic dyes, such as alizarin dyes, azo dyes or metal phthalocyanine dyes, or nutrients or trace nutrients, such as salts of iron, manganese, boron, copper, cobalt, molybdenum or zinc.

Stabilizers, such as low-temperature stabilizers, preservatives, antioxidants, light stabilizers or other agents which improve chemical, biological, and/or physical stability may also be present. Additionally present may be foam-formers or defoamers.

Furthermore, the formulations and application forms derived from them, may also comprise, as additional auxiliaries, adherents such as carboxymethylcellulose, natural and synthetic polymers in powder, granule or latex form, such as gum arable, polyvinyl alcohol, polyvinyl acetate, or natural phospholipids, such as cephalins or lecithins, or synthetic phospholipids. Further possible auxiliaries include mineral or vegetable oils.

There may possibly be further auxiliaries present in the formulations and the application forms derived from them. Examples of such additives include fragrances, protective colloids, binders, adhesives, thickeners, thixotropic substances, penetrants, retention promoters, stabilizers, sequestrants, complexing agents, humectants or spreaders.

Suitable retention promoters include any of those substances which reduce the dynamic surface tension, such as dioctyl sulphosuccinate, or increase viscoelasticity, such as hydroxypropylguar polymers, for example.

Suitable penetrants in the present context include all those substances which are typically used in order to enhance the penetration of active agrochemical compounds into plants. Penetrants in this context are defined in that, from a (generally aqueous) application liquor and/or from a spray coating, they are able to penetrate the cuticle of the plant and thereby increase the mobility of one or more active compounds in the cuticle. This property can be determined using the method described in the literature (Baur et al., 1997, Pesticide Science 51, 131-152). Examples include alcohol alkoxylates such as coconut fatty ethoxylate or isotridecyl ethoxylate, fatty acid esters such as rapeseed or soybean oil methyl esters, fatty amine alkoxylates such as taliowamine ethoxylate, or ammonium and/or phosphonium salts such as ammonium sulphate or diammonium hydrogen phosphate, for example.

The formulations can comprise between 0.00000001% and 98% or 99% by weight of active component or, between 0.01% and 95% by weight of active component, or between 0.5% and 90% by weight of active component, based on the weight of the formulation. The content of the active component is defined as the sum of *Bacillus* bacteria or product thereof and *Collimonas* bacteria or product thereof.

The active component content of the application forms (crop protection products) prepared from the formulations may vary within wide ranges. The active compound concentration of the application forms may be situated typically between 0.00000001% and 95% by weight of active component, or between 0.00001% and 1% by weight, based on the weight of the application form. Application can be performed in a customary manner adapted to the application forms.

Generally speaking, the active components may be combined with any solid or liquid additive commonly used for formulation purposes. Typically, the formulation additives are selected from those additives that do not inactivate the active components. For example, additives that do not inactivate *Bacillus* or *Collimonas* present in a composition, or products thereof, may be used in the formulations described herein.

III. Methods

Compositions or formulations as described above can be applied to a plant to reduce overall damage of plants and plant parts as well as losses in harvested fruits or vegetables caused by fungal or oomycetous phytopathogens. In some cases, a composition or formulation described above can be applied to a plant to increase resistance to a fungal or oomycetous pathogen. In some cases, the composition as described above can be applied to a plant to increase the overall plant health.

The term "plant health" generally refers various aspects of plant growth or resistance to external insults. For example, a plant with increased plant health may exhibit one or more of the following improved crop characteristics including: emergence, crop yields, protein content, oil content, starch content, more developed root system, improved root growth, improved root size maintenance, improved root effectiveness, improved stress tolerance (e.g., against drought, heat, salt, UV, water, cold), reduced ethylene (reduced production and/or inhibition of reception), tillering increase, increase in plant height, bigger leaf blade, less dead basal leaves, stronger tillers, greener leaf color, pigment content, photosynthetic activity, less input needed (such as fertilizers or water), less seeds needed, more productive tillers, earlier flowering, early grain maturity, less plant verse (e.g., less lodging), increased shoot growth, enhanced plant vigor, increased plant stand and early and better germination.

The effect of a composition according to the present invention on plant health as defined herein can be determined by comparing plants which are grown under the same environmental conditions, whereby a part of said plants is treated with a composition according to the present invention and another part of said plants is not treated with a composition according to the present invention. In some cases, said other part is not treated at all, treated with a placebo (e.g., an application without a composition according to the invention such as an application with only *Bacillus* or only *Collimonas*). In some cases, said other part is treated with a conventional treatment with a known efficacy.

A composition according to the present invention can be applied in any desired manner, such as in the form of a seed coating, soil drench, and/or directly in-furrow and/or as a foliar spray and applied either pre-emergence, post-emergence or both. The composition can be applied to the seed, the plant or to harvested fruits and vegetables or to the planting media (e.g., soil) wherein the plant is growing or wherein it is desired to grow. In some cases, the composition is applied during, before, or shortly after, transfer of the plant from one planting media to another. For example, a plant may be grown in a greenhouse until it reaches a certain stage, harvested, treated, and transferred to a field. A composition described herein can be applied to a conventional or transgenic plant.

In some embodiments, a composition containing *Bacillus* or a product thereof can be contacted with a plant and simultaneously or sequentially a composition containing a

*Collimonas* can be contacted with the plant. The contacting can be performed by a wide variety of methods known in the art.

In some cases, the plant is contacted with a formulation containing a *Collimonas* or product thereof and a *Bacillus* or product thereof formulated into a single, stable composition with an agriculturally acceptable shelf life. In some cases, one or more compositions or components are combined before or at the time of use. In some cases, a formulation is in a single "ready-mix" form. In some cases, the formulation is a combined spray mixture composed from solo-formulations that are combined during the application process, such as in a "tank mix" formulation. In some case, one or more components of the composition are combined when they are contacted with a plant in a sequential manner, i.e., one after the other within a reasonably short period, such as a few hours or days, e.g., 0.5, 1, or 2 hours to 7 days. The order of applying the composition according to the present invention is not essential for working the present invention.

Contacting a composition or formulation containing a composition described herein to a plant can be performed using a wide variety of customary treatment methods. For example the plant can contacted by dipping, coating, seed coating, spraying, atomizing, irrigating, evaporating, dusting, fogging, broadcasting, foaming, painting, spreading-on, watering (drenching), soil injection, or drip irrigating.

The amount of composition or formulation that is contacted with the plant depends on the final formulation, the size or type of the plant, plant parts, seeds, harvested fruits and vegetables to be treated, and the nature of the fungal or oomycetous pathogen, or degree of infection. In one embodiment a composition is contacted with a plant, the composition containing a *Bacillus* bacteria in a concentration of at least $10^5$ colony forming units per gram preparation (e.g., cells/g preparation, spores/g preparation), such as $10^5$-$10^{12}$ cfu/g, $10^6$-$10^{11}$ cfu/g, $10^7$-$10^{10}$ cfu/g, or $10^9$-$10^{10}$ cfu/g at the time point of applying biological control agents on a plant or plant parts such as seeds, fruits or vegetables. In one embodiment a composition is contacted with a plant, the composition containing a *Collimonas* bacteria in a concentration of at least $10^5$ colony forming units per gram preparation (e.g., cells/g preparation, spores/g preparation), such as $10^5$-$10^{12}$ cfu/g, $10^6$-$10^{11}$ cfu/g, $10^7$-$10^{10}$ cfu/g, or $10^9$-$10^{10}$ cfu/g at the time point of applying biological control agents on a plant or plant parts such as seeds, fruits or vegetables.

The *Collimonas* or a product thereof and *Bacillus* or a product thereof, can be used or employed in a synergistic ratio (e.g., by weight, mass, colony forming units, or cells per unit volume). The synergistic ratios can be determined routine methods. These ratios can refer to the ratio within a combined-formulation as well as to the ratio when both components are applied as mono-formulations to a plant to be treated.

In one embodiment the synergistic ratio of *Bacillus* bacteria to *Collimonas* bacteria lies in the range of 1:1000 to 1000:1, in the range of 1:500 to 500:1, in the range of 1:100 to 100:1, in the range of 1:10 to 10:1, in the range of 1:2 to 2:1, or about 1:1. In this context such ratios refer to a ratio of the number of cells or colony forming units of *Bacillus* over the number of cells or colony forming units of *Collimonas* bacteria contacted to a plant.

In one embodiment of the present invention, the concentration of *Collimonas* or *Bacillus* after dispersal is at least 50 g/ha, such as 50-7500 g/ha, 50-2500 g/ha, 50-1500 g/ha; at least 250 g/ha, at least 500 g/ha or at least 800 g/ha. The application rate of composition to be employed or used according to the present invention may vary. The skilled person is able to find the appropriate application rate by way of routine experiments.

In some embodiments, one or more compositions of the present invention are contacted with a plant by applying the composition to a seed. In some cases, the seed is contacted with *Bacillus* or a product thereof. In some cases, the seed is contacted with *Collimonas* or a product thereof. In some cases, the seed is contacted with *Bacillus* or a product thereof and *Collimonas* or a product thereof. In some cases, the seed is treated at different times with *Bacillus* or a product thereof and then *Collimonas* or a product thereof. In some cases, the seed is treated at different times with *Collimonas* or a product thereof and then *Bacillus* or a product thereof. In some cases, one or more individual compositions, or components thereof, of the invention may be present in different layers on the seed. In some cases, following treatment with the composition of the invention, the seed is subjected to a film-coating process in order to prevent dust abrasion of the seed.

A composition of the invention can be applied alone or in a suitable formulation to the seed. The seed can be treated in a condition such that no damage occurs in the course of the treatment. Generally speaking, the seed may be treated at any point in time between harvesting and sowing. Typically, seed is used which has been separated from the plant and has had cobs, hulls, stems, husks, hair or pulp removed. Thus, for example, seed may be used that has been harvested, cleaned and dried to a moisture content of less than 15% by weight. Alternatively, seed can also be used that after drying has been treated with water, for example, and then dried again.

When treating seed it is necessary, generally speaking, to ensure that the amount of the composition of the invention, and/or of other additives, that is applied to the seed is selected such that the germination of the seed is not adversely affected, and/or that the plant which emerges from the seed is not damaged. This is the case in particular with active ingredients which may exhibit phytotoxic effects at certain application rates.

The compositions of the invention can be applied in the form of a suitable formulation to the seed. Suitable formulations and methods for seed treatment are known to the skilled person and are described in, for example, the following documents; U.S. Pat. No. 4,272,417; U.S. Pat. No. 4,245,432; U.S. Pat. No. 4,808,430; U.S. Pat. No. 5,876,739; US 2003/0176428; WO 2002/080675; or WO 2002/0281 86, the contents of which are hereby incorporated in their entirety for all purposes.

The application rate of the seed-dressing formulations which can be used in accordance with the invention may be varied within a relatively wide range. It is guided by the particular amount of the *Bacillus* or products thereof or by the particular amount of *Collimonas* or products thereof, by the nature of the fungal or oomycetous pathogen, by the seed, or combinations thereof.

Compositions of the present invention can be contacted with a plant to protect the plant from phytopathogenic fungi or Oomycetes. Such phytopathogenic fungi or Oomycetes include, but are not limited to, soilborne pathogens, which include members of the classes Plasmodiophoromycetes, Peronosporomycetes, (Syn, Oomycetes), Chytridiomycetes, Zygomycetes, Ascomycetes, Basidiomycetes and Deuteromycetes (Syn. Fungi imperfecti). The compositions can be used in plant protection as foliar, seed dressing or soil fungicide. Furthermore, they are suitable for combating fungi or Oomycetes, which inter alia infest wood or roots of plant.

Non-limiting examples of pathogens of fungal diseases which can be treated in accordance with the invention include: diseases caused by powdery mildew pathogens, for example *Blumeria* species, for example *Blumeria graminis*; *Podosphaera* species, for example *Podosphaera leucotricha*; *Sphaerotheca* species, for example *Sphaerotheca fuliginea*; or *Uncinula* species, for example *Uncinula necator*.

One or more compositions of the invention can be contacted with a plant to control diseases caused by rust disease pathogens, for example *Gymnosporangium* species, for example *Gymnosporangium sabinae*; *Hemileia* species, for example *Hemileia vastatrix*; *Phakopsora* species, for example *Phakopsora pachyrhizi* and *Phakopsora meibomiae*; *Puccinia* species, for example *Puccinia recondite, P. triticina, P. graminis*, or *P. striiformus*; or *Uromyces* species, for example *Uromyces appendiculatus*.

One or more compositions of the invention can be contacted with a plant to control diseases caused by pathogens from the group of the Oomycetes, for example *Albugo* species, for example *Algubo Candida*; *Bremia* species, for example *Bremia lactucae*; *Peronospora* species, for example *Peronospora pisi* or *P. brassicae*; *Phytophthora* species, for example *Phytophthora infestans*; *Plasmopara* species, for example *Plasmopara viticola*; *Pseudoperonospora* species, for example *Pseudoperonospora humuli* or *Pseudoperonospora cubensis*; or *Pythium* species, for example *Pythlum ultimum*.

One or more compositions of the invention can be contacted with a plant to control leaf blotch diseases and leaf wilt diseases caused, for example, by *Alternaria* species, for example *Alternaria solani*; *Cercospora* species, for example *Cercospora beticola*; *Cladiosporium* species, for example *Cladiosporium cucumerinum*; *Cochliobolus* species, for example *Cochliobolus sativus, Cochliobolus miyabeanus*; *Colletotrichum* species, for example *Colletotrichum lindemuthianum*; *Cycloconium* species, for example *Cycloconium oleaginum*; *Diaporthe* species, for example *Diaporthe citri*; *Elsinoe* species, for example *Elsinoe fawcettii*; *Gloeosporium* species, for example *Gloeosporium laeticolor*; *Glomerella* species, for example *Glomerella cingulata*; *Gulgnardia* species, for example *Gulgnardia bidwelli*; *Leptosphaeria* species, for example *Leptosphaeria maculans, Leptosphaeria nodorum*; *Magnaporthe* species, for example *Magnaporthe grisea*; *Microdochium* species, for example *Microdochium nivale*; *Mycosphaerella* species, for example *Mycosphaerella graminicola, M. arachidicola* and *M. fijiensis*; *Phaeosphaeria* species, for example *Phaeosphaeria nodorum*; *Pyrenophora* species, for example *Pyrenophora teres*; *Ramularia* species, for example *Ramularia collocygni*; *Rhynchosporium* species, for example *Rhynchosporium secalis*; *Septoria* species, for example *Septoria apii*; *Typhula* species, for example *Typhula incarnate*; or *Venturia* species, for example *Venturia inaequalis*.

One or more compositions of the invention can be contacted with a plant to control root and stem diseases caused, for example, by *Corticium* species, for example *Corticium graminearum*; *Fusarium* species, for example *Fusarium oxysporum*; *Gaeumannomyces* species, for example *Gaeumannomyces graminis*; *Rhizoctonia* species, such as, for example *Rhizoctonia solani*; *Tapesia* species, for example *Tapesia acuformis*; or *Thielaviopsis* species, for example *Thielaviopsis basicola*.

One or more compositions of the invention can be contacted with a plant to control ear and panicle diseases (including corn cobs) caused, for example, by *Alternaria* species, for example *Alternaria* spp.; *Aspergillus* species, for example *Aspergillus flavus*; *Cladosporium* species, for example *Cladosporium cladosporioides*; *Claviceps* species, for example *Claviceps purpurea*; *Fusarium* species, for example *Fusarium culmorum*; *Gibberella* species, for example *Gibberella zeae*; *Monographella* species, for example *Monographella nivalis*; or *Septoria* species, for example *Septoria nodorum*.

One or more compositions of the invention can be contacted with a plant to control diseases caused by smut fungi, for example *Sphacelotheca* species, for example *Sphacelotheca reiliana*; *Tilletia* species, for example *Tilletia caries, T. controversa*; *Urocystis* species, for example *Urocystis occulta*; or *Ustilago* species, for example *Ustilago nuda*, or *U. nuda tritici*.

One or more compositions of the invention can be contacted with a plant to control fruit rot caused, for example, by *Aspergillus* species, for example *Aspergillus flavus*; *Botrytis* species, for example *Botrytis cinerea*; *Penicillium* species, for example *Penicillium expansum* and *P. purpurogenum*; *Sclerotinia* species, for example *Sclerotinia sclerotiorum*; or *Verticilium* species, for example *Verticilium alboatram*.

One or more compositions of the invention can be contacted with a plant to control seed- and soil-borne rot and wilt diseases, and also diseases of seedlings, caused, for example, by *Fusarium* species, for example *Fusarium culmorum*; *Phytophthora* species, for example *Phytophthora cactorum*; *Pythium* species, for example *Pythium ultimum*; *Rhizoctonia* species, for example *Rhizoctonia solani*; or *Sclerotium* species, for example *Sclerotium rolfsii*.

One or more compositions of the invention can be contacted with a plant to control cancers, galls and witches' broom caused, for example, by *Nectria* species, for example *Nectria galligena*; or wilt diseases caused, for example, by *Monilinia* species, for example *Monilinia laxa*.

One or more compositions of the invention can be contacted with a plant to control deformations of leaves, flowers and fruits caused, for example, by *Taphrina* species, for example *Taphrina deformans*.

One or more compositions of the invention can be contacted with a plant to control degenerative diseases of woody plants caused, for example, by *Esca* species, for example *Phaeomoniella chlamydospora, Phaeoacremonium aleophilum*, or *Fomitiporia mediterranea*.

One or more compositions of the invention can be contacted with a plant to control diseases of flowers and seeds caused, for example, by *Botrytis* species, for example *Botrytis cinerea*; diseases of plant tubers caused, for example, by *Rhizoctonia* species, for example *Rhizoctonia solani*; or *Helminthosporium* species, for example *Helminthosporium solani*.

The following diseases can be controlled using one or more compositions of the present invention: Fungal diseases on leaves, stems, pods and seeds caused, for example, by *Alternaria* leaf spot (*Alternaria* spec. *atrans tenuissima*), Anthracnose (*Colletotrichum gloeosporoides dematium* var. *truncatum*), brown spot (*Septoria glycines*), cercospora leaf spot and blight (*Cercospora kikuchii*), Choanephora leaf blight (*Choanephora infundibulifera trispora* (Syn.)), dactuliophora leaf spot (*Dactuliophora glycines*), downy mildew (*Peronospora manshurica*), drechslera blight (*Drechslera glycini*), frogeye leaf spot (*Cercospora sojina*), leptosphaerulina leaf spot (*Leptosphaerulina trifolii*), phyllostica leaf spot (*Phyllosticta sojaecola*), pod and stem blight (*Phomopsis sojae*), powdery mildew (*Microsphaera diffusa*), pyrenochaeta leaf spot (*Pyrenochaeta glycines*), rhizoctonia aerial, foliage, and web blight (*Rhizoctonia solani*), rust (*Phakopsora pachyrhizi, Phakopsora meibomiae*), scab (*Sphaceloma glycines*), stemphylium leaf blight (*Stemphylium botryosum*), target spot (*Corynespora cassiicola*).

Fungal diseases on roots and the stem base caused, for example, by black root rot (*Calonectria crotalariae*), charcoal rot (*Macrophomina phaseolina*), fusarium blight or wilt, root rot, and pod and collar rot (*Fusarium oxysporum, Fusarium orthoceras, Fusarium semitectum, Fusarium equiseti*), mycoleptodiscus root rot (*Mycoleptodiscus terrestris*), neocosmospora (*Neocosmospora vasinfecta*), pod and stem blight (*Diaporthe phaseolorum*), stem canker (*Diaporthe phaseolorum* var. *caulivora*), phytophthora rot (*Phytophthora megasperma*), brown stem rot (*Phialophora gregata*), pythium rot (*Pythium aphanidermatum, Pythium irregulare, Pythium debaryanum, Pythium myriotylum, Pythium ultimum*), rhizoctonia root rot, stem decay, and damping-off (*Rhizoctonia solani*), sclerotinia stem decay (*Sclerotinia sclerotiorum*), sclerotinia southern blight (*Sclerotinia rolfsii*), thielaviopsis root rot (*Thielaviopsis basicola*).

Plants which can be treated in accordance with the invention include the following main crop plants: maize, soya bean, cotton, *Brassica* oil seeds such as *Brassica napus* (e.g. canola), *Brassica rapa, B. juncea* (e.g. (field) mustard) and *Brassica carinata*, rice, wheat, sugar beet, sugar cane, oats, rye, barley, millet and sorghum, triticale, flax, grapes and various fruit and vegetables from various botanic taxa, for example Rosaceae sp. (for example pome fruits such as apples and pears, but also stone fruits such as apricots, cherries, almonds and peaches, and berry fruits such as strawberries), Ribesioidae sp., Juglandaceae sp., Betulaceae sp., Anacardiaceae sp., Fagaceae sp., Moraceae sp., Oleaceae sp., Actimidaceae sp., Lauraceae sp., Musaceae sp. (for example banana trees and plantations), Rubiaceae sp. (for example coffee), Theaceae sp., Sterculiceae sp., Rutaceae sp. (for example lemons, oranges and grapefruit); Solanaceae sp. (for example tomatoes, potatoes, peppers, aubergines), Liliaceae sp., Compositae sp. (for example lettuce, artichokes and chicory-including root chicory, endive or common chicory), Umbelliferae sp. (for example carrots, parsley, celery and celeriac), Cucurbitaceae sp. (for example cucumbers-including gherkins, pumpkins, watermelons, calabashes and melons), Alliaceae sp. (for example leeks and onions), Cruciferae sp. (for example white cabbage, red cabbage, broccoli, cauliflower, Brussels sprouts, pak choi, kohlrabi, radishes, horseradish, cress and chinese cabbage), Leguminosae sp. (for example peanuts, peas, and beans—for example common beans and broad beans), Chenopodiaceae sp. (for example Swiss chard, fodder beet, spinach, beetroot), Malvaceae (for example okra), Asparagaceae (for example asparagus); useful plants and ornamental plants in the garden and woods; and in each case genetically modified types, varietals, or cultivars of these plants.

EXAMPLES

The following examples are offered to illustrate, but not to limit the claimed invention.

Example 1

Antifungal and Antioomycete Properties of *Collimonas* Isoaltes and their Use in Synergy-Based Biocontrol of *Fusarium* Wilt I. Introduction The bacterial genus *Collimonas* (Leveau, J. H., S. Uroz, et al. (2010) *Environmental Microbiology* 12(2): 281-292) comprises three described species: *C. fungivorans, C. pratensis*, and *C. arenae* (de Boer, W., J. H. J. Leveau, et al. (2004) *International Journal of Systematic and Evolutionary Microbiology* 54: 857-864; Hoppener-Ogawa, S., W. de Boer, et al. (2008) *International Journal of Systematic and Evolutionary Microbiology* 58: 414-419). Collimonads have antifungal (de Boer, W., P. J. A. Klein Gunnewiek, et al. (1998) *Soil Biology & Biochemistry* 30(2): 193-203; Mela, F., K. Fritsche, et al. (2011) *ISME J* 5(9): 1494-1504), mycophagous (de Boer, W., P. J. A. Klein Gunnewiek, et al. (2001) *Applied and Environmental Microbiology* 67(8): 3358-3362), chitinolytic (Leveau, J. H. J., S. Gerards, et al. (2006) *Journal of Microbiological Methods* 66(2): 276-285), and weathering (Uroz, S., C. Calvaruso, et al. (2009) *Soil Biology & Biochemistry* 41(10): 2178-2186) properties. *C. fungivorans* Ter331 is the best characterized *Collimonas* strain so far: its genome sequence is available (Mela, F., K. Fritsche, et al. (2008) *FEMS Microbiology Ecology* 66(1): 45-62; Mela, F., K. Fritsche, et al. (2011) *ISME J* 5(9): 1494-1504; Mela, F., K. Fritsche, et al. (2012) *Environmental Microbiology Reports* 4(4): 424-432), its chitinolytic system has been elucidated (Fritsche, K., W. de Boer, et al. (2008) *FEMS Microbiology Ecology* 66(1): 123-135), and it was shown to be *rhizosphere*-competent and to protect tomato plants from developing symptoms upon infection with *Fusarium oxysporum* f. sp. *radicis-lycopersici* which causes *Fusarium* crown and root rot on tomato (Kamilova, F., J. H. J. Leveau, et al. (2007) *Environmental Microbiology* 9(6): 1597-1603). Strain Ter331 was one of several so-called Ter strains that were isolated from dune soils on the Dutch island of Terschelling (de Boer, W., P. J. A. Klein Gunnewiek, et al. (1998) *Soil Biology & Biochemistry* 30(2): 193-203). Since then, the presence of collimonads has been reported from many other parts of the world (Offre, P., B. Pivato, et al. (2008) *FEMS Microbiology Ecology* 65(2): 180-192; Postma, J., M. T. Schilder, et al. (2008) *Soil Biology & Biochemistry* 40(9): 2394-2406; Axelrood, P. E., M. L. Chow, et al. (2002) *Canadian Journal of Microbiology* 48(7): 655-674; Chow, M. L., C. C. Radomski, et al. (2002) *FEMS Microbiology Ecology* 42(3): 347-357. Project Collifornia was launched in 2009 to discover *Collimonas* strains native to California. Here, we provide a characterization of these Cal strains in terms of antifungal and antioomycete activity in vitro. We show that strain *C. arenae* Cal35 was by far the most effective in these confrontation assays. We also demonstrate that in a greenhouse setting a mixture of *C. arenae* Cal35 and the commercially available, *Bacillus*-based biofungicide Serenade Soil, but not Cal35 alone or Serenade Soil alone, can reduce disease symptoms on tomato plants that were challenged with *Fusarium oxysporum* f. sp. *lycopersicum* (Fol), causative agent of *Fusarium* wilt. We refer to this synergy-based emerging property as 'biocombicontrol'.

II. Materials and Methods

Microorganisms Used in this Study.

*Collimonas* strains Ter6, Ter10, Ter14, Ter91 and Ter331 have been described elsewhere (de Boer, W., P. J. A. Klein Gunnewiek, et al. (1998) *Soil Biology & Biochemistry* 30(2): 193-203; de Boer, W., J. H. J. Leveau, et al. (2004) *International Journal of Systematic and Evolutionary Microbiology* 54: 857-864; Hoppener-Ogawa, S., W. de Boer, et al. (2008) *International Journal of Systematic and Evolutionary Microbiology* 58: 414-419). *Collimonas* strains Cal1 and Cal2 were isolated from soil near Berry Creek, Calif., while Cal31, Cal35, and Cal39 were isolated from forest soil at the Jughandle Reserve, Mendocino County, Calif. (Uroz, S., J. J. Tech, et al. (2013) *Biology & Biochemistry*, in press). The methods for isolating and identifying *Collimonas* isolates have been described in detail elsewhere (Uroz, S., J. J. Tech, et al. (2013) *Biology & Biochemistry*, in press). In short, soil samples were inoculated into Tryptic Soy Broth containing natamycin and nalidixic acid, incubated at 20° C. for 3 days while shaking, after which an aliquot was transferred to chitin broth for an additional incubation at 20° C. for 7 days. In parallel, soil samples were seeded directly into chitin broth. Aliquots of chitin broth enrichments were spread onto colloidal chitin agar plates, and incubated at 20° C. for 7 days. Colonies with a halo of cleared chitin were selected and analyzed using a *Collimonas*-specific probe assay (Hoppener-Ogawa et al., Appl Environ Microbiol. 2007 July; 73(13):4191-7). Positive isolates were further tested by a Restriction Fragment Length Polymorphism (RFLP) assay on amplified 16S rRNA genes using the BstBI restriction enzyme, which is specific for the identification of *Collimonas* (Hoppener-Ogawa et al., Appl Environ Microbiol. 2007 July; 73(13):4191-7). Positive isolates were confirmed to be *Collimonas* and assigned to one of the three described species by DNA sequencing of PCR-amplified 16S rRNA genes using primers pA and 1492r. An additional *Collimonas* strain, *Collimonas* sp. D-25, was a kind gift from Yoichiro Hirose and was originally isolated from forest *rhizosphere* soil in Japan. Fungi and Oomycetes were gifts from various faculty members in the Department of Plant Pathology at UC Davis. Many of them cause disease on economically important crops and trees. For the greenhouse experiments (see below), two different strains of *Fusarium oxysporum* f. sp. *lycopersici* (Fol) race 3 were used. Strain D11 was originally isolated from infected tomato plants on a commercial field in Yolo County, Calif., and had been in storage on sterile filter paper since 2010. Strain D12 was isolated in 2012 from infected plants in San Joaquin County, Calif. Isolation of Fol was achieved by washing stems of diseased plants with anti-bacterial hand soap (Dial Gold), and cutting diagonally to produce 0.25-cm thick pieces which were surface sterilized in 0.6% sodium hypochloride (10% bleach) for 1 minute, and placed on Acidified Potato Dextrose Agar (APDA) plates for 5 days at 25° C. with an 8-hour photoperiod (48 W fluorescence light bulbs, Lights of America, model 8045E, Los Angeles, Calif.). After 5 days, hyphal tips of colonies presenting *Fusarium*-like macroconidia were transferred to fresh APDA plates and incubated for another 7 days. From the resulting colonies, single spores were transferred to individual APDA plates. DNA was extracted from 30 mg of hyphal mass with the DNeasy Plant Mini Kit (Qiagen, Valencia, Calif.) and used in a PCR with *Fusarium*-specific primers EF-1 (5'-ATGGG-TAAGGAAGACAAGAC-3') and EF-2 (5'-GGAAGTAC-CAGTGATCATGTT-3'). The PCR was conducted in final volumes of 50 µl per reaction, using 10 ng of template DNA, 0.2 mM of each dNTP, 0.2 µM of each primer, and 0.25 units of GoTaq DNA polymerase. The following PCR cycling conditions were used: 40 cycles of 30 sec. at 95° C., 30 sec. at 55° C., and 1 min at 72° C., then followed by 5 min. at 72° C. The PCR products were visualized on 1.5% TBE agarose gels. Tests of pathogenicity and race differentiation were performed with tomato cultivars Early Pak 7 (susceptible), VFN-8 (resistant to race 1), Walter (resistant to race 1 and 2), and AB 319 (resistant to race 1, 2, and 3).

Confrontation Assays.

To test the antagonistic activity of collimonads (n=11) and control bacteria (n=2) against our set of fungi and Oomycetes (n=22), we used a confrontation setup that has been described previously by Mela, F., K. Fritsche, et al. (2011) *ISME J* 5(9): 1494-1504. This involved streaking the bacteria against spores or a plug of fungus or oomycete on Water Yeast Agar (WYA) supplemented with 2 mM N-acetylglucosamine. To score the antagonistic activity of each bacterial strain against every one of the fungi/Oomycetes, we used a scale from 1 to 5, where 1 represents strong inhibition and 5 represents complete lack of inhibition (FIG. 1). In total, we looked at 286 pairwise confrontations (13 bacterial strains×22 fungal/oomycetal strains). Each confrontation assay was performed in triplicate, and a mean score was calculated for each pair. To calculate an 'antifungal/antioomycete' score for any given bacterial strain, we averaged the mean scores over all 22 fungi/Oomycetes tested against that strain. To calculate a '*Collimonas*-susceptibility' score for any given fungus/oomycete, we averaged the mean scores over all 11 *Collimonas* strains tested against that fungus/oomycete.

Greenhouse Experiments.

In total, we performed 4 independent greenhouse experiments to test if and by how much *C. arenae* Cal35, Serenade Soil, or a mixture of Cal35 and Serenade Soil could reduce the weight loss and vascular discoloration that result from infection of tomato seedlings with Fol D11 or D12. Fungal spore suspensions were prepared fresh from one-week-old APDA cultures of Fol. The colonized plates were flooded with 15 mL of autoclaved deionized water, then conidia were scraped off using a sterile glass slide and filtered through four layers of sterile cheesecloth. The conidial concentration was determined with a Neubauer Levy Ultra Plane Hemacytometer (Hausser Scientific, Horsham, Pa.) and adjusted to $10^6$ per ml with autoclaved deionized water. *C. arenae* Cal35 was streaked from −80° C. freezer stock onto King's B agar and incubated at 24° C. for 5 days. Plates were then flooded with 15 mL of autoclaved deionized water and bacterial biomass was scraped off with a sterile glass slide. Serial dilutions were made of this suspension, read for optical density at 600 nm ($OD_{600}$) using a Genesys 10S UV-Vis spectrophotometer (Thermo Scientific, Wilmington, Del.), and adjusted to $10^6$ cells per ml using autoclaved deionized water. Suspensions of Serenade Soil (Agraquest, Davis Calif.) were prepared by 1000-fold dilution of the liquid product (containing $10^9$ colony-forming units of *Bacillus* per gram, as per the label) in water. Mixtures of Cal35 and Serenade Soil (referred to as Collinade) were prepared just prior to use in the experiments by mixing equal volumes of Serenade Soil suspension and *C. arenae* Cal 35 suspension.

Figure 2:
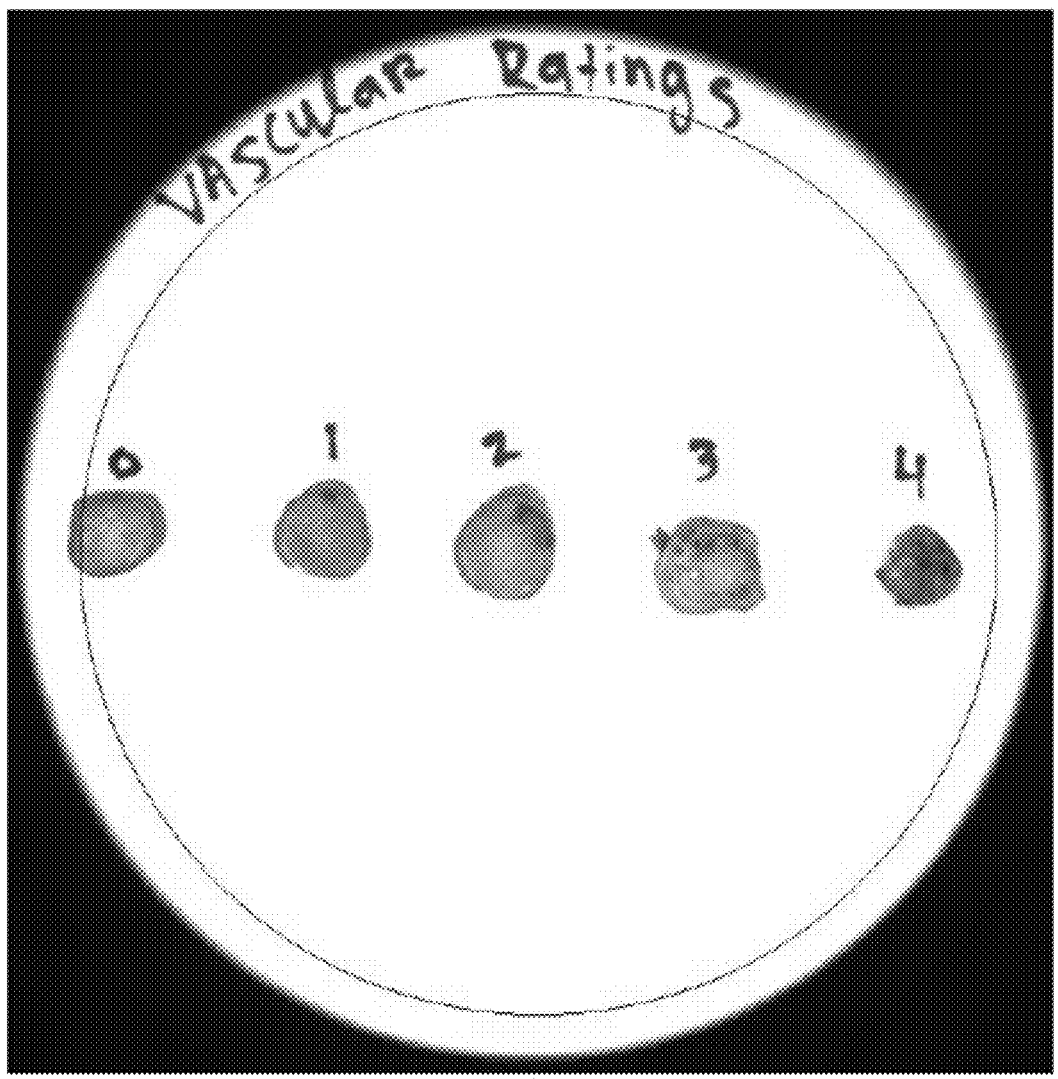
FIG. 2. Representative photographs of tomato stems showing various degrees of vascular discoloration: 0, no discoloration; 1, discoloration of <5% of the stem cross section; 2, 5-20% discoloration; 3, 20-40% discoloration; 4, >40% discoloration.

Tomato seeds (Early Pak 7) were sown in the greenhouse in containers with UC potting soil mix (50% sphagnum peat moss, 50% washed sand, and per cubic meter-2.43 kg of dolomite lime, 0.872 kg oyster shell lime, 0.872 kg superphosphate, 0.344 kg calcium nitrate, 135 ml potassium nitrate, and 90 ml potassium sulfate). After 11 days, seedlings (two true leaves) were gently removed from the soil, root-dipped for 4 minutes in water, Cal35 suspension, Serenade Soil suspension, or Collinade, then transferred to fresh UC potting soil mix, and placed back in the greenhouse. After one week, seedling roots were dug up again and dipped for 4 minutes in either water or FOL conidial suspension, then transplanted into containers with fresh UC potting soil mix. After 3 days, 100 ml of water or Cal35, Serenade Soil, or Collinade were poured onto the soil surrounding the crown of the tomato plant. One week later, this drench was repeated. Four weeks after the root inoculation with Fol, individual tomato plants were cut at the soil line to determine shoot dry weight and to assess vascular discoloration in the stem on a scale of 0-4 (see FIG. 2: 0, no vascular discoloration; 1, <5% discoloration, typically light brown; 2, 5-20% discoloration, typically light brown; 3, 20-40% discoloration, typically dark brown; 4, >40% discoloration, typically dark brown). Data were analyzed using SAS version 5.1.2600 (SAS Institute, Inc. Cary N.C.). Plants were grown in the greenhouse in a randomized complete block design, with 6 replicates per treatment in experiment 1, 10 replicates in experiments 2 and 3, and 15 replicates in experiment 4.

Field Trial.

We designed and carried out a field trial during the 2014 growing season at the Armstrong Plant Pathology Field Station at UC Davis. Tomato plants (Heinz 5508, resistant to Fol race 1 and 2 but not race 3, also resistant to *Verticillium dahliae* race 1 and Tomato Spotted Wilt Virus) were seeded in 128-cell seedling trays with 3.5×3.5×6.5 cm cells and kept in the greenhouse for three weeks, at which time trays were dipped for 4 minutes in one of the following four solutions (prepared as described above): 1) water, 2) Cal35 suspension, 3) Serenade Soil suspension, or 4) Collinade. Dipped trays were placed back in the greenhouse and after one week, tomato plants were hand-transplanted (May 17, 2014) 30 cm apart into a drip-irrigatable plot with a randomized complete block design (five single-row 92-cm beds with 60-cm between-row spacing beds, plus a pair of border rows) featuring 20 blocks with 30 plants each: 8 of these blocks were planted with water-dipped seedlings, 4 with Cal35-dipped seedlings, 4 with Serenade Soil-dipped seedlings, and 4 with Collinade-dipped seedlings. Immediately after planting, 10 liters of Fol spore suspension were delivered by drip to all blocks except for 4 of the blocks planted with the water-dipped seedlings; these blocks represent the no-Fol treatment. The spore solution was prepared as described above. After one week, 10 liters of water, Cal35 suspension, Serenade Soil suspension, or Collinade were drip-delivered into each one of the corresponding blocks (e.g., Cal35 suspension was delivered into the blocks that were planted with Cal35-dipped seedlings, and water into the blocks with water-dipped seedlings). One week later, this injection was repeated. The field was watered as needed through the drip. Fertilizer UN-32 was applied through the drip once a week until flowering, at 75 ml per block and starting 12 days after transplanting. Plants also received a one-time application of Miracle-Gro Quick Start (Scotts Miracle-Gro, Marysville, Ohio) 5 days after transplanting, at 450 ml per block. Weeding was done manually, no herbicides or pesticides were used. Fruits were harvested on Sep. 19, 2014 (4 months after planting), at which time more than 90 percent of the fruit were ripe. Vascular discoloration and shoot dry weight (after removal of the fruit, see below) were determined for 15 plants in the center of each block, as described above. Also measured for these 15 plants combined were the weight of red, green, sunburn, and moldy fruit. Marketable yield was calculated from red fruit weight, and expressed in tons per acre.

III. Results

We tested 11 strains of *Collimonas* (Table 1) in standardized confrontation assays (Mela, F., K. Fritsche, et al. (2011) ISME J5(9): 1494-1504) to assess and compare their impact on mycelial growth of 22 fungi or Oomycetes (Table 2). *Collimonas* strains belonged to one of the three known species (*C. arenae, fungivorans* or *pratensis*), and included 5 of the original Ter isolates, in addition to 5 isolates recovered from Californian soils and a Japanese strain *Collimonas* sp. D-25. We also included two negative controls, i.e. *E. coli* TOP 10 (Invitrogen) and *P. putida* 1290 (Leveau, J. H. J., and S. E. Lindow. (2005) *Applied and Environmental Microbiology*, 71(5): 2365-2371; Leveau, J. H. J. and S. Gerards. (2008) *FEMS Microbiology Ecology* 65(2): 238-250). In total, 286 bacterium-fungus/oomycete pairs were evaluated in triplicate on Water Yeast Agar (WYA) plates supplemented with 2 mM N-acetylglucosamine as described before (Mela, F., K. Fritsche, et al. (2011) *ISME J* 5(9): 1494-1504) and scored on a scale from 1 (near-complete inhibition of mycelial growth) to 5 (complete lack of inhibition of mycelial growth) as shown in FIG. 1.

TABLE 1

Bacterial strains used in this study and tested for their ability to inhibit mycelial growth.

| Genus | Species | Strain[a] | Score[a] |
|---|---|---|---|
| Collimonas | arenae | Cal35 | 1.75 ± 0.89 |
| Collimonas | fungivorans | Ter14 | 2.06 ± 0.99 |
| Collimonas | fungivorans | Ter6 | 2.30 ± 1.01 |
| Collimonas | fungivorans | Cal2 | 2.30 ± 1.21 |
| Collimonas | fungivorans | Cal1 | 2.37 ± 1.12 |
| Collimonas | fungivorans | Cal39 | 2.47 ± 1.11 |
| Collimonas | pratensis | Ter91 | 2.75 ± 1.12 |
| Collimonas | arenae | Ter10 | 2.84 ± 1.00 |
| Collimonas | sp. | D-25 | 2.90 ± 1.59 |
| Collimonas | fungivorans | Ter331 | 2.91 ± 1.10 |
| Collimonas | pratensis | Cal31 | 3.04 ± 1.10 |
| Pseudomonas | putida | 1290 | 5.02 ± 0.24 |
| Escherichia | coli | TOP10 | 5.06 ± 0.27 |

[a]Shown is the average and standard deviation of all mean scores (each mean score calculated from 3 replicate assays per fungus/oomycete) for each bacterial strain in confrontation with 22 tested fungi/Oomycetes.
Scoring was done as shown in FIG. 1: 1 means near-complete inhibition while 5 means no inhibition at all.
Strains are ranked according to their score.

TABLE 2

Fungi and Oomycetes used in this study and their relative susceptibility to growth inhibition by *Collimonas* strains.

| Phylum | Class | Order | Family | Genus | Species | Score[a] |
|---|---|---|---|---|---|---|
| Ascomycota | Saccharomycetes | Saccharomycetales | Dipodascaceae | Geotrichum | candidum[1] | 1.05 ± 0.17 |
| | Eurotiomycetes | Eurotiales | Trichocomaceae | Aspergillus | niger[2] | 1.42 ± 0.55 |
| | | | | | carbonarius[3] | 2.50 ± 1.06 |
| | Dothideomycetes | Pleosporales | Pleosporaceae | Alternaria | alternata[4] | 2.77 ± 0.66 |
| | | Botryosphaeriales | Botryosphaeriaceae | Botryosphaeria | stevensii[5] | 2.36 ± 1.11 |
| | Sordariomycetes | Hypocreales | — | Fusarium | circinatum[6] | 3.91 ± 0.30 |
| | | | | | oxysporum[7] | 3.27 ± 0.65 |
| | | | Glomerellaceae | Colletotrichum | acutatum[8] | 2.84 ± 0.81 |
| | | Magnaporthales | Magnaporthaceae | Magnaporthe | grisea[9] | 2.76 ± 0.73 |
| | | Phyllachorales | — | Verticillium | dahliae[10] | 2.33 ± 0.92 |
| | | Diaporthales | Cryphonectriaceae | Cryphonectria | parasitica[11] | 1.91 ± 0.79 |
| | Leotiomycetes | Helotiales | Sclerotiniaceae | Botrytis | cinerea[12] | 1.04 ± 0.13 |
| | | | | Monilinia | fructicola[13] | 1.00 ± 0.00 |
| Basidiomycota | Agaricomycetes | Atheliales | Atheliaceae | Sclerotium | rolfsii[14] | 2.27 ± 0.91 |
| | | | | | cepivorum[15] | 1.64 ± 1.12 |
| | | Cantharellales | Ceratobasidiaceae | Rhizoctonia | solani[16] | 3.09 ± 0.92 |

TABLE 2-continued

Fungi and Oomycetes used in this study and their relative susceptibility to growth inhibition by *Collimonas* strains.

| Phylum | Class | Order | Family | Genus | Species | Score[a] |
|---|---|---|---|---|---|---|
| Heterokontophyta | Oomycetes | Pythiales | Pythiaceae | *Pythium* | violae[17] | 3.14 ± 1.28 |
| | | | | | irregulare[18] | 2.36 ± 1.13 |
| | | | | | ultimum[19] | 3.17 ± 1.16 |
| | | Peronosporales | Pythiaceae | *Phytophthora* | capsici[20] | 3.09 ± 0.94 |
| | | | | | cactorum[21] | 4.00 ± 0.00 |
| Zygomycota | Zygomycetes | Mucorales | Mucoraceae | *Mucor* | sp.[22] | 3.46 ± 0.69 |

[a]Shown is the average and standard deviation of all mean scores (each mean score calculated from 3 replicate assays per *Collimonas* strain) for each fungal/oomycetal strain in confrontation with 11 tested collimonads. Scoring was done as shown in FIG. 1: 1 means near-complete inhibition while 5 means no inhibition at all.
[1]causative agent of sour rot on fruits and vegetables;
[2]model strain CBS120.49;
[3]sour rot of grape;
[4]tomato mold;
[5]tree cankers;
[6]pitch canker of pine;
[7]f. sp. *lycopersici*, race 3, tomato wilt;
[8]fruit rot;
[9]rice blast;
[10]*Verticillium* wilt of tomato;
[11]chestnut blight;
[12]bunch rot of grape;
[13]brown rot of peach;
[14]Southern blight;
[15]*Allium* root rot;
[16]damping off disease;
[17]cavity spot of carrot;
[18/19]damping off disease of carrot;
[20]rot of bell pepper;
[21]root rots;
[22]common soil fungus.

Averaged over all tested fungi/Oomycetes (Table 1), the inhibitory performance was greatest for strain C. arenae Cal 35 (score=1.75), followed by C. fungivorans Ter14 (2.06) and C. fungivorans Cal 2 (2.30). Strain Cal35 was unique and superior among the tested *Collimonas* strains in that it was the only one to near-completely inhibit the growth of *Sclerotium rolfsii* and *Rhizoctonia solani* as well as the Oomycetes *Pythium violae, Pythium ultimum*, and *Phytophthora capsici*. It shared with C. fungivorans Ter14 the ability to inhibit *Pythium irregulare*. Strain Cal35 was also the sole best inhibitor of *Fusarium circinatum, Fusarium oxysporum*, and *Mucor* sp. The overall least affected by co-inoculation with *Collimonas* bacteria (Table 2) were the fungus *Fusarium circinatum* (score=3.9) and the oomycete *Phytophthora cactorum* (4.0). Three fungi were near-completely inhibited (<1.7) by all *Collimonas* strains tested, i.e. Moniliniafructicola, *Botrytis cinerea*, and *Geotrichum candidum*. All three are known as important postharvest pathogens of fruits, including tomato. None of the fungi tested were negatively affected by E. coli or P. putida (>4.50). In some cases, fungal growth actually seemed to be stimulated by the presence of E. coli or P. putida (e.g. as was the case for *Phytophthora capsici*).

Figure 3:
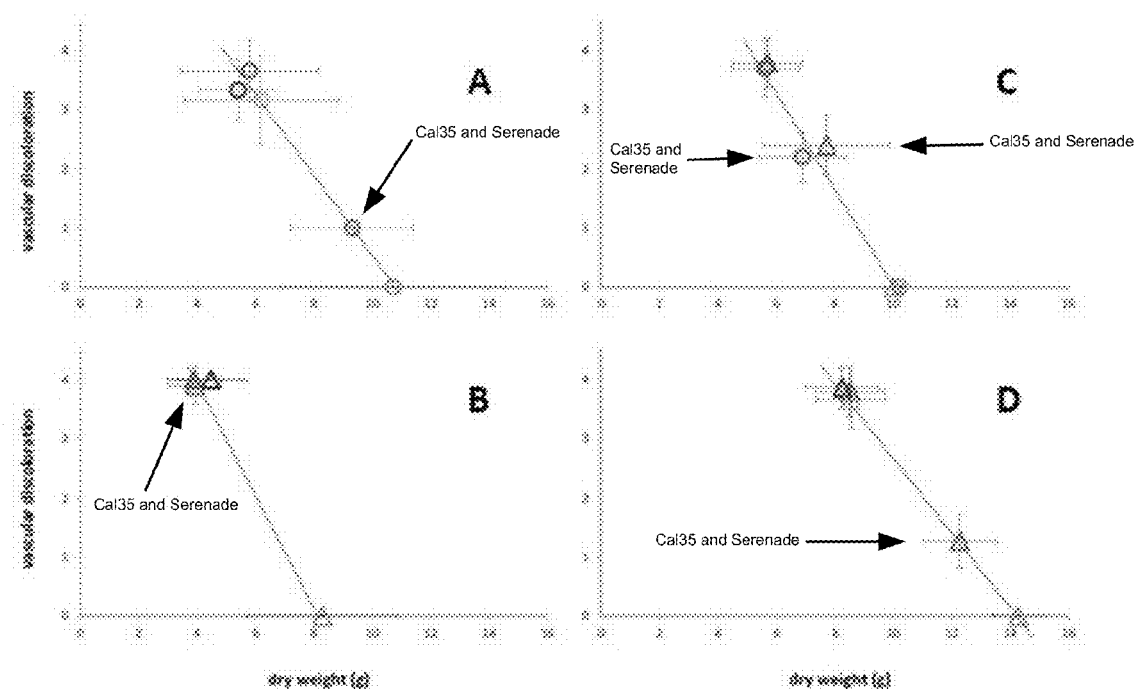
FIG. 3. Dry weight (shoot) and vascular discoloration (0-4 scale) of greenhouse-grown, Fol-challenged tomato plants that were treated with a mixture of Cal35 and Serenade Soil, Cal35 only, Serenade Soil only, or that were untreated. Data points with a y-axis value of zero represent the control plants (no Fol). Panels A through D represent 4 independent experiments, which were carried out in A) April/May 2012 (high/low greenhouse temperatures of 31/16° C.), B) June/July 2012 (33/17° C.), C) December 2012/January 2013 (29/15° C.). Data points for treatment with Cal35 and Serenade soil in panels A, C, and D have a significantly lower vascular discoloration score than the other treatment data points.

C. arenae strain Cal35 was selected for further experiments to test the hypothesis that its in vitro observed antifungal activity predicts its potential as a biocontrol agent to protect plant roots against fungal pathogens. In a first of 4 greenhouse experiments (FIG. 3A), when applied as a prophylactic root dip and subsequent soil drenches, Cal 35 was not able to suppress the effects of *Fusarium* wilt (measured as vascular discoloration and dry weight) on tomato plants that were root-dip inoculated with Fol race 3 isolate D11 (FIG. 3A, first and third circles from the top). In a control treatment with the commercial, *Bacillus*-based product Serenade Soil, we saw the same result (FIG. 3A, second circle from the top). However, when Cal35 was applied as a 1:1 mixture with Serenade Soil, we observed a significant reduction in vascular discoloration and a decrease in dry weight loss (FIG. 3A, fourth circle from the top). In two independent repetitions of this experiment with another Fol isolate (D12), we achieved the same result in one of the experiments (FIG. 1D); in the other (FIG. 3B), the Cal35-Serenade Soil mixture had no effect. During the latter experiment, greenhouse temperatures were higher than in any of the other greenhouse trials; possibly, this was the reason for biocontrol failure in this case. A fourth greenhouse experiment featured both D11 and D12, and again we observed protection of the tomato seedlings from Fol with the Cal35/Serenade Soil mixture, but not Cal35 alone or Serenade Soil alone (FIG. 3C).

Figure 4:
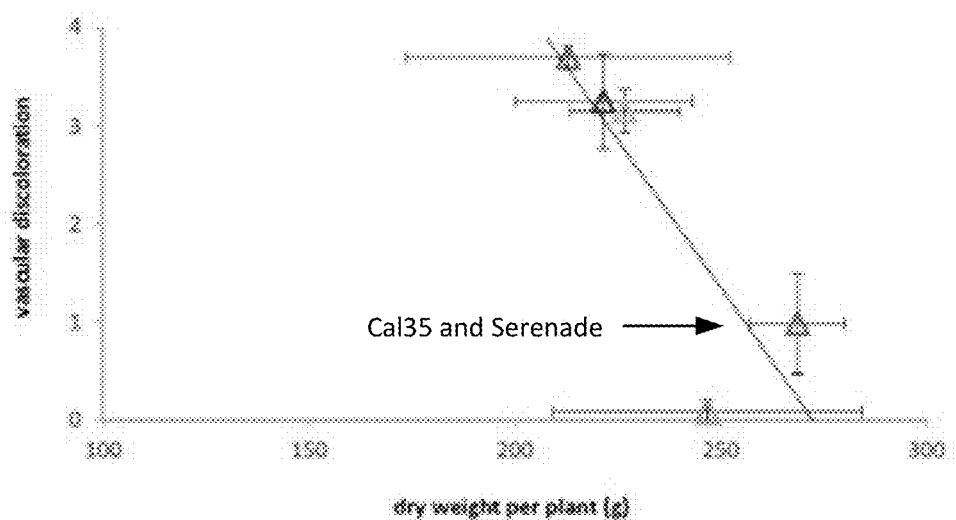
FIG. 4. Dry weight and vascular discoloration (0-4 scale) of field-grown, harvest-ready Fol-challenged tomato plants that were treated with a mixture of Cal35 and Serenade Soil, Cal35 only, Serenade Soil only, or that were untreated. Green data points represent the control plants (no Fol). Experiment was carried out in Summer 2014. Data points for treatment with Cal35 and Serenade soil have a significantly lower vascular discoloration score than the other treatment data points.
Figure 5:
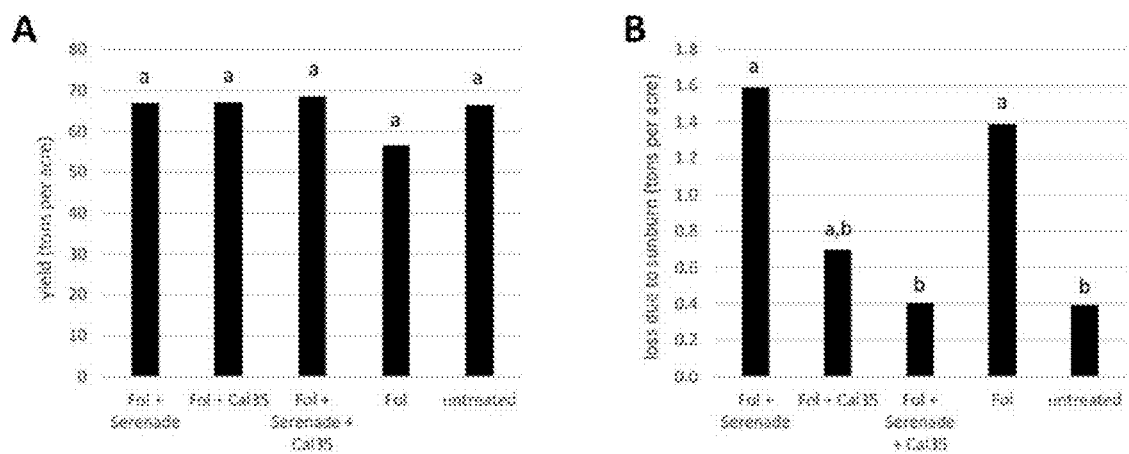
FIG. 5. Marketable yield (A) and yield loss due to sunburn (B), in tons per acre, at time of harvest, from the field experiment described in the text and in FIG. 2. Bars labeled with the same letter in either panel A or panel B were not significantly different from each other.

In a controlled trial at the Plant Pathology Field Station at UC Davis which was designed to replicate the greenhouse experiments in a field setting, we observed the same synergistically Collinade protection from Fol-induced symptoms, i.e. vascular discoloration and dry weight loss (FIG. 4). Vascular discoloration in the Collinade treatment was significantly reduced compared to Cal35 alone (p=0.00024) or Serenade (p=0.00067) alone. Similarly, the Collinade treatment yielded a significantly higher shoot dry weight (after removal of the fruit) than Cal35 alone (p=0.0032) or Serenade alone (p=0.0084). Marketable fruit yield was highest with Collinade (68.3 tons per acre), but this value did not differ significantly from other treatments, including the no-Fol control, at 56.3 tons per acre (FIG. 5A). However, we did observe (FIG. 5B) significantly less (approximately 1 ton per acre) of sunburn-related loss of yield in Fol-challenged plots that received Collinade, compared to Fol-challenged plots that received Serenade alone (p=0.046) or no treatment (p=0.0[43]).

IV. Conclusion

This study demonstrates and compares the antifungal and antioomycete activities of *Collimonas* strains isolated from Californian soils. The in vitro data suggest not only variation in the ability of individual *Collimonas* strains to inhibit or slow down the mycelial growth of fungi and/or Oomycetes, but also in the relative susceptibility of fungal/oomycetal strains to confrontation with *Collimonas*. In greenhouse and field experiments, we were able to demonstrate a synergistic effect between *C. arenae* Cal35 and Soil Serenade which protected tomato plants from Fol symptoms including vascular discoloration and dry weight loss. In the field experiment, we saw no statistically significant impact of Fol on marketable yield, but we did observe a protective effect from sunburn damage. We suspect that this is related to our observation (not shown) of a thicker canopy in the Collinade-treated blocks which would better protect the developing fruit from sun exposure. A thicker canopy also explains the higher shoot dry weight, which in turn follows from the ability of Collinade to prevent vascular infection by Fol. While the mechanisms underlying the observed synergism between Cal35 and Serenade Soil are unknown still, the data seem to suggest that there is enormous potential for improvement of the efficacy of already existing products such as Serenade Soil through combination with bacteria such as *Collimonas* to achieve biocombicontrol of plant diseases.

Example 2

Soil Sample Analysis of Collimonads

A total of 24 soil samples were analyzed for the presence of collimonads. These samples were taken as triplicates from 8 agricultural fields in California that were planted with tomatoes, almonds, alfalfa, strawberry, wheat, lettuce, onion or carrot. Analysis was performed using an enrichment protocol as described before. In short, one gram from each soil sample was resuspended in 10 mL of 1× Basic Salt Solution (de Boer, W., Klein Gunnewiek, P. J. A., Lafeber, P., Janse, J. D., Spit, B. E., Woldendorp, J. W., 1998, Anti-fungal properties of chitinolytic dune soil bacteria. Soil Biology and Biochemistry. 30, 193-203) by vortexing at maximum speed for 45 seconds. One milliliter of each suspension was inoculated into 50 ml of tryptic soy broth (Oxoid) with 50 mg natacid and 30 mg nalidixic acid per liter and incubated at 20° C. for 3 days at 200 rpm, after which a 100-µl aliquot was transferred to 50 mL of chitin broth (modified from de Boer, W., Leveau, J. H. J., Kowalchuk, G. A., Klein Gunnewiek, P. J. A., Abeln, E. C. A., Figge, M. J., Sjollema, K., Janse, J. D., van Veen, J. A., 2004, *Collimonas fungivorans* gen. nov., sp. nov., a chitinolytic soil bacterium with the ability to grow on living fungal hyphae. International Journal of Systematic and Evolution Microbiology 54, 857-864, excluding the agar) supplemented with 50 mg natacid and 30 mg nalidixic acid per liter for an additional incubation at 20° C. for 7 days at 200 rpm. In parallel, one milliliter of the original soil suspension was inoculated directly into 50 ml of chitin broth supplemented with 50 mg natacid and 30 mg nalidixic acid per liter and incubated at 20° C. for 7 days at 200 rpm. Ten microliters of the chitin broth enrichments were spread in duplicate onto chitin agar plates (de Boer, W., Leveau, J. H. J., Kowalchuk, G. A., Klein Gunnewiek, P. J. A., Abeln, E. C. A., Figge, M. J., Sjollema, K., Janse, J. D., van Veen, J. A., 2004, *Collimonas fungivorans* gen. nov., sp. nov., a chitinolytic soil bacterium with the ability to grow on living fungal hyphae. International Journal of Systematic and Evolution Microbiology 54, 857-864), and incubated at 20° C. for 7 days. Colonies with a halo of cleared chitin were shown to be negative in a *Collimonas*-specific probe assay (Hoppener-Ogawa, S., Leveau, J. H., Smant, W., van Veen, J. A., de Boer, W., 2007. Specific detection and real-time PCR quantification of potentially mycophagous bacteria belonging to the genus *Collimonas* in different soil ecosystems. Applied and Environmental Microbiology. 73, 4191-4197). This result was confirmed by a Restriction Fragment Length Polymorphism (RFLP) assay on amplified 16S rRNA genes using the BstBI restriction enzyme, which is specific for the identification of *Collimonas* (Hoppener-Ogawa, S., Leveau, J. H., Smant, W., van Veen, J. A., de Boer, W., 2007. Specific detection and real-time PCR quantification of potentially mycophagous bacteria belonging to the genus *Collimonas* in different soil ecosystems. Applied and Environmental Microbiology. 73, 4191-4197) and by DNA sequencing of PCR amplified 16S rRNA genes using primers pA (Edwards, U., Rogall, T., Blocker, H., Emde, M., Bottger, E. C. 1989. Isolation and direct complete nucleotide determination of entire genes. Characterisation of a gene coding for 16S ribosomal RNA. Nucleic Acids Research. 17, 7843-7853) and 1492r (Lane, D. J., 1991. 16S/23S rRNA sequencing, p. 115-176. In E. Stackebrandt M. Goodfellow (ed.), Nucleic acid techniques in bacterial systematics. John Wiley and Sons, Chichester, United Kingdom). In conclusion, bacteria from the genus *Collimonas* in these soil samples were undetectable by the methods employed.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

What is claimed is:
1. A method of cultivating a plant comprising:
 a). contacting said plant with bacteria of the genus *Collimonas*; and
 b). contacting said plant with bacteria of the genus *Bacillus*,
 wherein said contacting of a) in combination with said contacting of b) causes a synergistic antifungal or synergistic anti-oomycete effect against a fungal or an oomycetous infection.
2. The method of claim 1, wherein part of said plant contacted with bacteria of the genus *Collimonas* is a root of said plant.
3. The method of claim 1, wherein part of said plant contacted with bacteria of the genus *Bacillus* is a root of said plant.
4. The method of claim 1, wherein part of said plant contacted with bacteria of the genus *Collimonas* is a seed of said plant.
5. The method of claim 1, wherein part of said plant contacted with bacteria of the genus *Bacillus* is a seed of said plant.
6. The method of claim 1, wherein part of said plant contacted with bacteria of the genus *Collimonas* is foliage of said plant.
7. The method of claim 1, wherein part of said plant contacted with bacteria of the genus *Bacillus* is foliage of said plant.
8. The method of claim 1, wherein the contacting of a) comprises contacting the plant with bacteria of the genus *Collimonas* and a product thereof.

9. The method of claim 1, wherein the contacting of b) comprises contacting the plant with bacteria of the genus *Bacillus* and a product thereof.

10. The method of claim 1, wherein the fungal or oomycetous infection comprises an infection by a fungal or oomycetous pathogen from a class selected from the group consisting of Plasmodiophoromycetes, Oomycetes, Chytridiomycetes, Zygomycetes, Ascomycetes, Basidiomycetes, Deuteromycetes, Sordariomycetes, and combinations thereof.

11. The method of claim 10, wherein the fungal or oomycetous pathogen is from the class Oomycetes.

12. The method of claim 1, wherein said fungal infection comprises infection by a fungal pathogen from a genus selected from the group consisting of *Fusarium, Geotrichum, Aspergillus, Alternaria, Botryosphaeria, Colletotrichum, Magnaporthe, Verticillium, Cryphonectria, Botrytis, Monilinia, Sclerotium, Rhizoctonia*, and combinations thereof.

13. The method of claim 1, wherein said fungal or oomycetous infection comprises infection by an Oomycete from a genus selected from the group consisting of *Pythium, Phytophthora*, and combinations thereof.

14. The method of claim 1, wherein said plant is a plant selected from the group consisting of tomato, potato, sweet potato, cassava, beets, ginger, horseradish, radish, *ginseng*, turnip, any root or tuber crop, pepper, eggplant, ground cherry, tomatillo, okra, other fruiting vegetables, cucumber cantaloupe, melon, muskmelon, squash, watermelon and other cucurbit plants.

15. The method of claim 1, wherein said bacteria of the genus *Bacillus* comprise *Bacillus subtilis*.

16. The method of claim 1, wherein said bacteria of the genus *Bacillus* comprise *Bacillus subtilis* var. *amyloliquefaciens*.

17. The method of claim 1, wherein said bacteria of the genus *Bacillus* comprise *Bacillus subtilis* QST 713.

18. The method of claim 1, wherein said bacteria of genus *Collimonas* comprise a species selected from the group consisting of *Collimonas arenae, Collimonas fungivorans*, and *Collimonas pratensis*.

19. The method of claim 1, wherein said bacteria of genus *Collimonas* comprise *C. arenae* Cal35.

20. The method of claim 1, wherein said bacteria of genus *Collimonas* comprise *C. arenae* Cal35 and said bacteria of the genus *Bacillus* comprise *Bacillus subtilis* QST 713.

21. The method of claim 1, wherein said bacteria of the genus *Collimonas* are in the form of a liquid suspension.

22. The method of claim 1, wherein said bacteria of the genus *Collimonas* are in a liquid suspension at a concentration of approximately $1 \times 10^6$ cells per milliliter.

23. The method of claim 1, wherein said bacteria of the genus *Bacillus* are in the form of a liquid suspension.

24. The method of claim 1, wherein said bacteria of the genus *Bacillus* are in a liquid suspension at a concentration of approximately $1 \times 10^8$ or $1 \times 10^9$ colony forming units per gram.

25. The method of claim 1, wherein said contacting of a) or b) comprises a root dip.

26. The method of claim 1, wherein said contacting of a) or b) comprises a soil drench.

27. An antifungal or an anti-oomycetous composition comprising:
 a). bacteria of the genus *Collimonas*; and
 b). bacteria of the genus *Bacillus*, wherein said a) and said b) together exhibits a synergistic antifungal or a synergistic anti-oomycetous effect.

28. The composition of claim 27, wherein the composition comprises bacteria of the genus *Collimonas* and a product thereof.

29. The composition of claim 27, wherein the composition comprises bacteria of the genus *Bacillus* and a product thereof.

30. The composition of claim 27, wherein said bacteria of the genus *Bacillus* comprise *Bacillus subtilis*.

31. The composition of claim 27, wherein said bacteria of the genus *Bacillus* comprise *Bacillus subtilis* QST 713.

32. The composition of claim 27, wherein said bacteria of genus *Collimonas* comprise a species selected from the group consisting of *Collimonas arenae, Collimonas fungivorans*, and *Collimonas pratensis*.

33. The composition of claim 27, wherein said bacteria of genus *Collimonas* comprise *C. arenae* Cal35.

34. The composition of claim 27, wherein said bacteria of genus *Collimonas* comprise *C. arenae* Cal35 and said bacteria of the genus *Bacillus* comprise *Bacillus subtilis* QST 713.

35. The composition of claim 27, wherein said bacteria of the genus *Collimonas* are in the form of a liquid suspension.

36. The composition of claim 27, wherein said bacteria of the genus *Collimonas* are in a liquid suspension with a concentration of approximately $1 \times 10^6$ cells per milliliter.

37. The composition of claim 27, wherein said bacteria of the genus *Bacillus* are in the form of a liquid suspension.

38. The composition of claim 27, wherein said bacteria of the genus *Bacillus* are in a liquid suspension with a concentration of approximately $1 \times 10^8$ or $1 \times 10^9$ colony forming units per gram.

39. The plant cultivated by the method of claim 1.

* * * * *